United States Patent [19]

Takasugi et al.

[11] Patent Number: 5,050,974
[45] Date of Patent: Sep. 24, 1991

[54] OPTICAL SYSTEM FOR ENDOSCOPES

[75] Inventors: Yoshiharu Takasugi, Iruma; Hiroyuki Fukuda, Hachioji, both of Japan

[73] Assignee: Olympus Optical Co., Ltd., Tokyo, Japan

[21] Appl. No.: 406,383

[22] Filed: Sep. 11, 1989

[30] Foreign Application Priority Data

Sep. 12, 1988 [JP] Japan .................. 63-226531

[51] Int. Cl.⁵ .................. B29D 11/00; G02B 17/00; G02B 9/60
[52] U.S. Cl. .................. 359/728; 359/708; 359/663
[58] Field of Search .................. 350/432, 465, 443

[56] References Cited

U.S. PATENT DOCUMENTS

| | | | |
|---|---|---|---|
| 4,403,837 | 9/1983 | Nakahashi | 350/465 |
| 4,662,725 | 5/1987 | Nisioka | 350/432 |
| 4,976,524 | 11/1990 | Chiba | 350/443 |
| 4,986,642 | 1/1991 | Yokota et al. | 350/432 |

FOREIGN PATENT DOCUMENTS 62-173415 7/1987 Japan .

*Primary Examiner*—Bruce Y. Arnold
*Assistant Examiner*—Rebecca D. Gass
*Attorney, Agent, or Firm*—Cushman, Darby & Cushman

[57] ABSTRACT

An optical system for endoscopes so adapted as to be usable with video endoscopes, comprising an imaging lens system equipped with an aperture stop and a field lens component arranged on the image side thereof, and so designed as to prevent the color shading from being produced by selecting an adequate focal length for the field lens component.

12 Claims, 20 Drawing Sheets

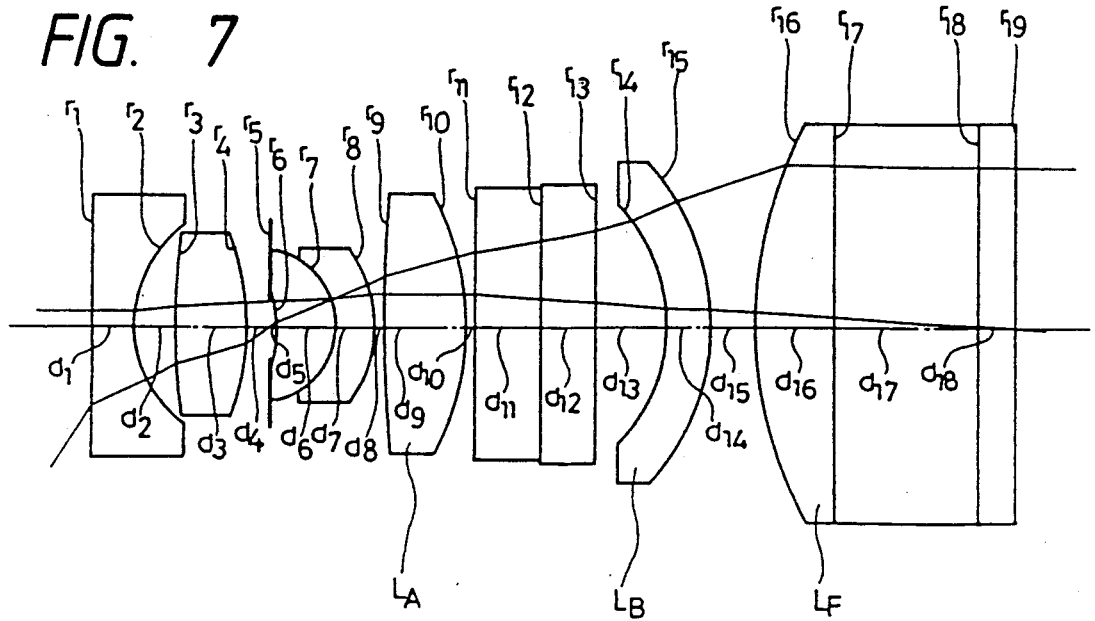
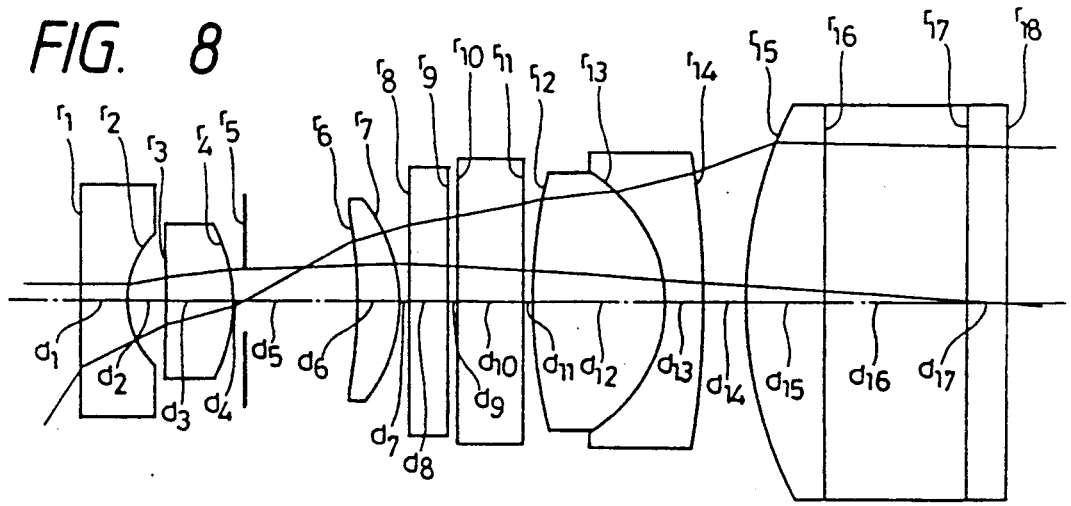
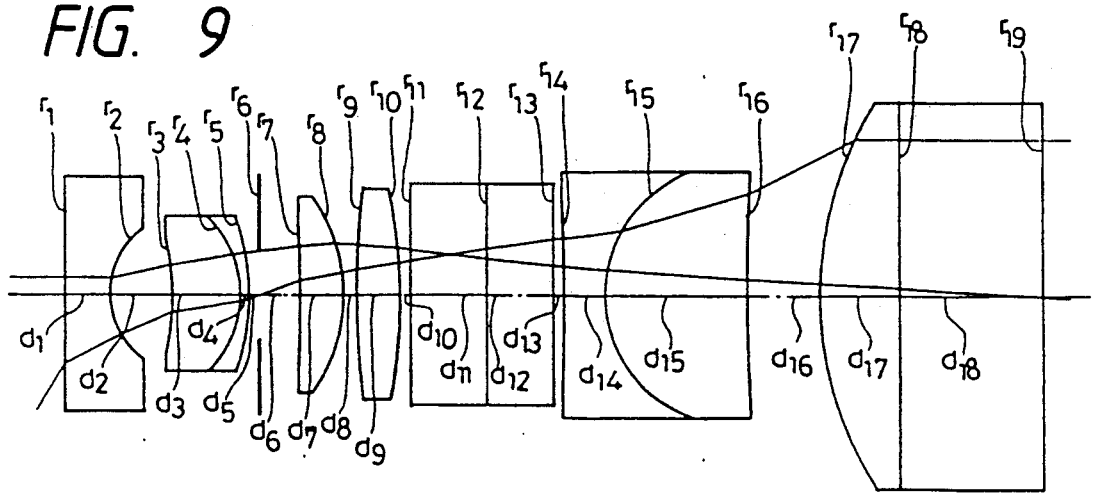

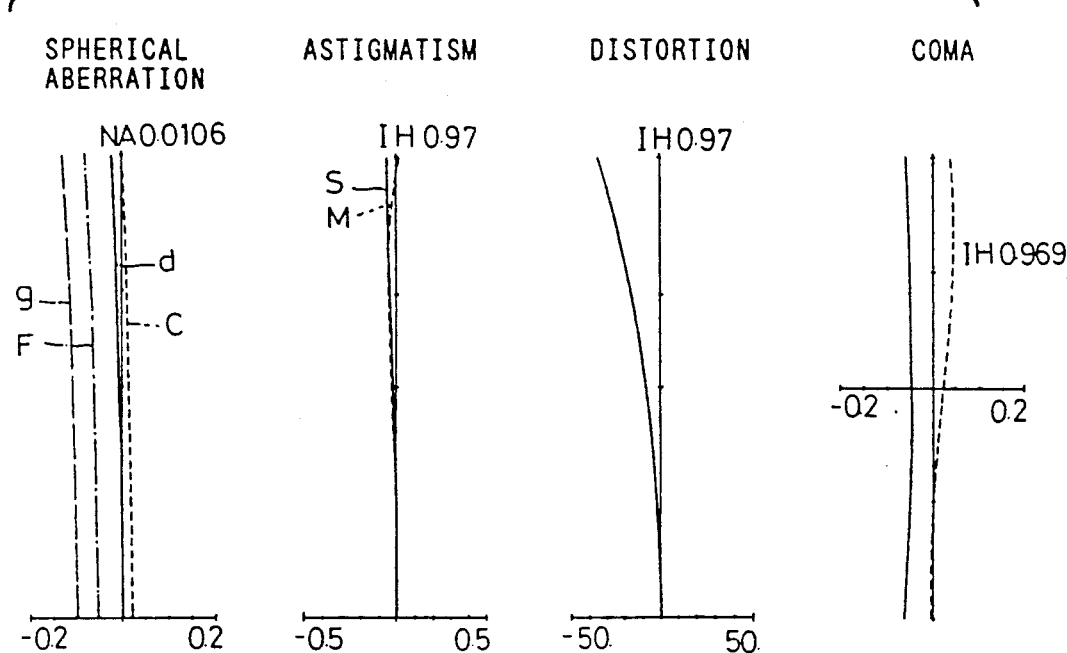
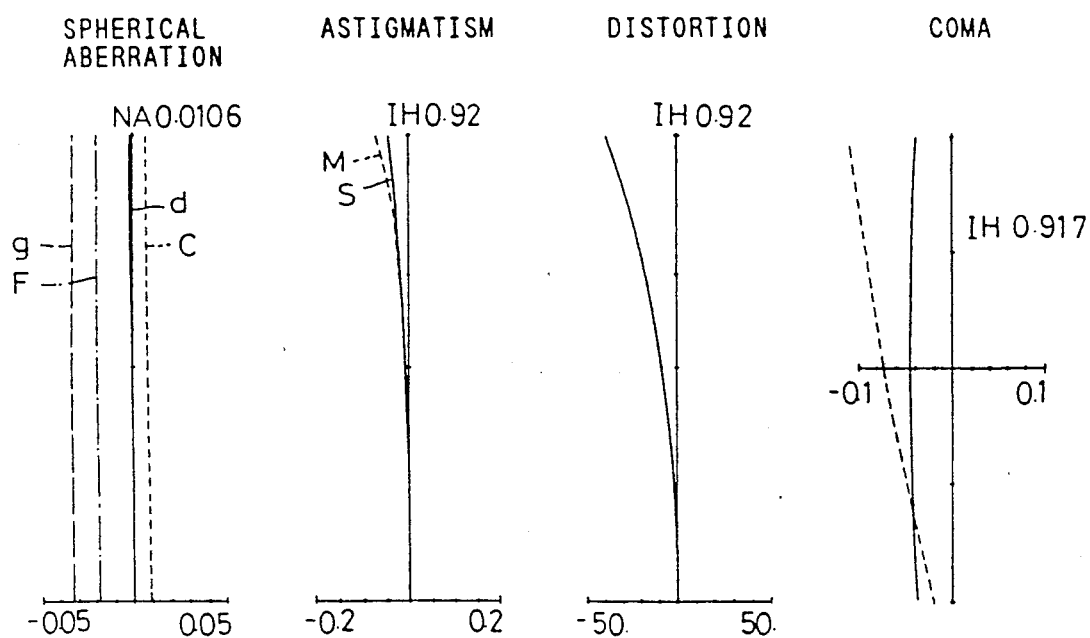

OPTICAL SYSTEM FOR ENDOSCOPES

BACKGROUND OF THE INVENTION a) Field of the Invention

The present invention relates to an imaging optical system for endoscopes.

b) Description of the Prior Art

Fiberscopes using image guide fiber bundles are practically employed in a large number as endoscopes. In the recent days, however, video endoscopes using various types of solid-state image pickup devices in place of the image guides are also used in a large number.

The video color imaging systems are classified roughly into the field sequential color system and the dot sequential color systems. The latter has a composition comprising a color encoding filter which is composed of mini-size color filters integrated in mosaic patterns corresponding to the picture elements of a solid-state image pickup device (usually referred to as the color mosaic filter). When a wide space is reserved between the filter and the light-receiving surface of the solid-state image pickup device, however, the light incident on the solid-stage image pickup device does not fall on the picture element on which the light is originally to fall after passing through the color encoding filter but on the neighboring picture element, thereby producing color ununiformity on an image (hereinafter referred to as the color shading). The color shading produced in this way cannot be avoided in an optical system of the same type as the optical system for endoscopes disclosed by Japanese Unexamined Published Patent Application No. 173415/62 wherein the principal ray 1 falls obliquely on an image pickup device I as shown in FIG. 1.

SUMMARY OF THE INVENTION

A primary object of the present invention is to provide an imaging optical system for endoscopes capable of forming an image free from the color shading even when the solid-state image pickup devices comprising the mosaic filters are used.

The optical system for endoscopes according to the present invention has the fundamental composition illustrated in FIG. 2 wherein a field lens component $L_F$ is arranged on the image side of an imaging lens system $L_M$ comprising an aperture stop S and a solid-state image pickup device is arranged on the side where rays emerge from said field lens component $L_F$. Further, the optical system for endoscopes according to the present invention is so designed as to satisfy the following condition (1):

$$f_F < 10f \quad (1)$$

wherein the reference symbol $f_F$ represents focal length of the field lens component $L_F$ and the reference symbol f designates focal length of the optical system as a whole.

By selecting the composition described above, the optical system according to the present invention is so adapted as to allow the principal ray to be incident nearly perpendicularly on the image surface thereof and therefore capable of preventing the color shading from being produced.

If the above-mentioned field lens component $L_F$ has too long a focal length, the optical system will have too long a total length and too large an outside diameter, thereby being unsuited for use with endoscopes. In order to make the optical system compact as a whole, it is desirable to design the optical system so as to satisfy the above-mentioned condition (1). If the condition (1) is not satisfied, the optical system will undesirably have too long a total length and too large an outside diameter.

The optical system for endoscopes according to the present invention comprises the field lens component $L_F$ arranged on the image side of the imaging lens system $L_M$ comprising the aperture stop and is so designed as to satisfy the condition (1). It is desirable to use, as at least one of the surfaces of the field lens component or in the vicinity thereof, an aspherical surface including portions whose refractive functions are gradually weakened as the portions are farther from the optical axis toward the margin.

The optical system according to the present invention is so adapted as to prevent the color shading by arranging the field lens component $L_F$ on the image side of the imaging lens system $L_M$ so that the principal ray is incident perpendicularly on the image surface thereof. In an ordinary optical system composed only of spherical lenses wherein rays are incident on the image surface thereof at different angles depending on image heights, it is desirable to arrange an aspherical surface in the vicinity of the field lens component so that angles of incidence of the rays are not different on the image surface.

When it is assumed that the rays are perpendicularly incident on the image surface at all the image heights in the optical system according to the present invention, tracing of the rays at all the image heights in the reverse direction toward the object side along the optical axis will clarify that all the rays pass through the center of the aperture stop. In other words, no spherical aberration is produced by the rays travelling from the image surface toward the object side along the optical axis in the telecentric optical system arranged on the image side of the aperture stop. Accordingly, it is desirable to arrange an aspherical surface at a location where spherical aberration is produced remarkably when tracing is made in the reverse direction from the image side, i.e., at a location in the vicinity of the field lens component $L_F$.

An optical system for endoscopes is generally designed as the retrofocus type consists of a front lens unit which has negative refractive power as a whole and is arranged on the object side of an aperture stop, and a rear lens unit which has positive refractive power as a whole and is arranged on the image side of the aperture stop. Normally, a positive lens component produces negative spherical aberration since it refracts rays more largely as the portions thereof become farther from the optical axis. It is therefore desirable to design the aspherical surface to be arranged in the vicinity of the field lens component $L_F$ so as to include portions whose refractive functions are gradually weakened as they are farther from the optical axis toward the margin.

The weakening of refractive function of a positive lens component means weakening of the converging function, i.e., the positive power thereof, whereas weakening of refractive function of a negative lens component means weakening of the diverging function, i.e., the negative power thereof.

When the optical system for endoscopes according to the present invention has a large field angle of approximately 100° or wider, barrel-shaped distortion is produced remarkably as image height increases. In order to correct this distortion, it is desirable to arrange, on the object side of the aperture stop, an aspherical surface having refractive function which is gradually weakened as the surface portions are farther from the optical axis toward the margin.

In order to correct distortion, it is sufficient to arrange an aspherical surface at a location at which the principal ray is high. For the above-described aspherical surface to be arranged in the vicinity of the field lens component $L_F$ in the optical system for endoscopes according to the present invention, however, a shape must be selected in such a manner that the rays at all the image heights are incident on an image pickup device at a definite angle (perpendicularly). It is therefore desirable to correct distortion by arranging the aspherical surface at a location at which rays are high on the object side of the aperture stop. The aspherical surface to be arranged for correcting distortion should include such portions as to gradually weaken the refractive function of the lens component as the portions are farther from the optical axis toward the margin.

The lens component which is located on the object side of the aperture stop and at which ray is the highest is the first lens component, and this lens component is usually designed as a negative lens component in an optical system for endoscopes. Remarkable distortion is produced by the object side surface of the first lens component (the first surface of the optical system) since said surface refracts rays outward more largely as the surface portions are farther from the optical axis toward the margin. When the first surface is designed as an aspherical surface including portions which weaken the refractive function of the lens component as the portions are farther from the optical axis toward the margin, for example, it is possible to correct distortion owing to the fact that the aspherical surface moderates refraction of the rays.

When only one aspherical surface is arranged on each of the object side and image side of the aperture stop, an attempt to correct distortion while keeping a definite angle of incidence on the image pickup device will produce astigmatism. Correction of this astigmatism will diversify the angle of incidence on the image pickup device, thereby making it impossible to correct aberrations sufficiently. For correcting the aberrations, it is desirable to use an additional aspherical surface.

Then, it is desirable to design the optical system for endoscopes according to the present invention so as to satisfy the following condition (2):

$$D_1 > 0.2f \qquad (2)$$

wherein the reference symbol $D_1$ represents the optical path length to be reserved between the aperture stop S and the field lens component $L_F$.

The solid-state image pickup device has sensitivity for the light having infrared wavelength and degrades color reproducibility on an image. In order to correct this defect, it is usually necessary to arrange an optical filter such as an infrared cut filter or the similar member in the optical path of the optical system. The condition (2) is required for arranging the optical member such as an optical filter. In order to arrange an optical filter having the desired characteristic, $D_1$ should desirably satisfy the condition (2). If the condition (2) is not satisfied, it will be difficult to arrange an optical filter in the optical system for endoscopes according to the present invention.

It is further desirable to design the optical system for endoscopes according to the present invention so as to satisfy the following condition (3):

$$0.2f < D_2 < 5f \qquad (3)$$

wherein the reference symbol $D_2$ represents optical path length as measured from the field lens component $L_F$ to the imaging surface, which should be measured from the vertex of the object side surface of the field lens component $L_F$ to the imaging surface when the field lens component $L_F$ is integrated with an image pickup device, or from the vertex of the image side surface of the field lens component $L_F$ to the imaging surface when the field lens component $L_F$ is separate from an image pickup device.

When $D_2$ has too small a value, it will be impossible to reserve a space for arranging, for example, an optical low pass filter for correcting moiré. If $D_2$ has too large a value, in contrast, it will be possible to reserve a space sufficient for arranging the optical low pass filter or the similar member, but the optical system will have too long a total length and cannot be compact.

When a plane parallel plate such as an optical filter is arranged on the object side of the field lens component $L_F$, i.e., in the imaging lens system, or between the imaging lens system and the field lens component $L_F$ in the optical system according to the present invention, the optical system is divided into a front subsystem located on the object side of the plane parallel plate and a rear subsystem located on the image side of the plane parallel plate. When two or more plane parallel plates are arranged in such a case, the optical system is to be divided into the front subsystem and the rear subsystem taking the plane parallel plate closest to the field lens component $L_F$ as a boundary. The front subsystem may be composed of a plural number of lens components including positive lens component(s) and negative lens component(s) for correcting aberrations. When the front subsystem has the above-described composition, it is desirable to design the subsystem so as to satisfy the following conditions (4), (5), and (6):

$$f_I > 0.3f \qquad (4)$$

$$|f_n| < 4f \qquad (5)$$

$$0.3f < f_p < 5f \qquad (6)$$

wherein the reference symbol $f_I$ represents focal length of the front subsystem, the reference symbol $f_n$ designates focal length of the negative lens components (not including the negative lens elements of the cemented doublets) and the reference symbol $f_p$ denote total focal length of the lens elements not including the negative lens element(s) arranged in the front subsystem.

The condition (4) defines focal length of the front subsystem. As $f_I$ becomes shorter, the optical path length is shorter between the front subsystem and the rear subsystem. If the condition (4) is not satisfied, it will therefore be impossible to arrange an optical filter.

If $f_n$ or $f_p$ exceeds the upper limit of the condition (5) or condition (6), the optical system will have too long a total length and too large an outside diameter, thereby making the optical system unsuited for use with endoscopes. If $f_p$ has a value smaller than the lower limit of the condition (6), in contrast, there will be available no space for arranging an optical filter.

BRIEF DESCRIPTION OF THE DRAWINGS

FIG. 2 through FIG. 24 show sectional views illustrating Embodiments 1 through 23 of the optical system for endoscopes according to the present invention;

FIG. 25 through FIG. 47 show curves illustrating aberration characteristics of the Embodiments 1 through 23 of the present invention.

DETAILED DESCRIPTION OF THE PREFERRED EMBODIMENTS

Figure 1:
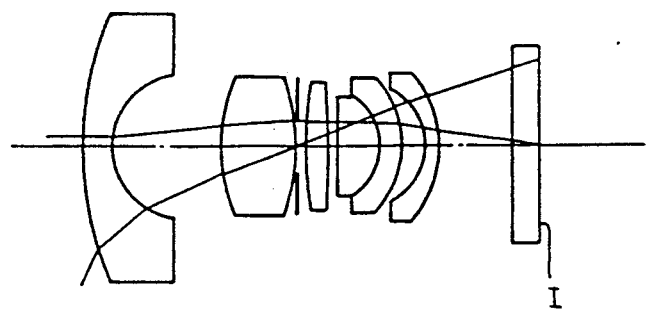
FIG. 1 shows a sectional view illustrating the conventional optical system for endoscopes.

Now, the present invention will be described more detailedly with reference to the accompanying drawings and the numerical data given below in the form of numerical data:

EMBODIMENT 1

| | | | |
|---|---|---|---|
| $f = 1.000$, | F/3.941, | $2\omega = 133.698°$ | |
| $IH = 1.0049$ | | | |
| $r_1 = \infty$ | | | |
| | $d_1 = 0.3045$ | $n_1 = 1.88300$ | $\nu_1 = 40.78$ |
| $r_2 = 0.5725$ | | | |
| | $d_2 = 0.2253$ | | |
| $r_3 = 2.9842$ | | | |
| | $d_3 = 0.3228$ | $n_2 = 1.84666$ | $\nu_2 = 23.78$ |
| $r_4 = -1.1924$ | | | |
| | $d_4 = 0.0609$ | | |
| $r_5 = \infty$ (stop) | | | |
| | $d_5 = 0.0609$ | | |
| $r_6 = -1.2314$ | | | |
| | $d_6 = 0.1827$ | $n_3 = 1.80518$ | $\nu_3 = 25.43$ |
| $r_7 = 1.6809$ | | | |
| | $d_7 = 0.6395$ | $n_4 = 1.51633$ | $\nu_4 = 64.15$ |
| $r_8 = -0.7893$ | | | |
| | $d_8 = 0.0609$ | | |
| $r_9 = 5.5341$ | | | |
| | $d_9 = 0.1583$ | $n_5 = 1.84666$ | $\nu_5 = 23.78$ |
| $r_{10} = 1.7381$ | | | |
| | $d_{10} = 0.8222$ | $n_6 = 1.51633$ | $\nu_6 = 64.15$ |
| $r_{11} = -1.7381$ | | | |
| | $d_{11} = 0.1279$ | | |
| $r_{12} = \infty$ | | | |
| | $d_{12} = 0.9135$ | $n_7 = 1.52000$ | $\nu_7 = 74.00$ |
| $r_{13} = \infty$ | | | |
| | $d_{13} = 0.2436$ | | |
| $r_{14} = 2.2400$ | | | |
| | $d_{14} = 0.7004$ | $n_8 = 1.51633$ | $\nu_8 = 64.15$ |
| $r_{15} = 19.9239$ | | | |
| | $d_{15} = 0.3045$ | | |
| $r_{16} = \infty$ | | | |
| | $d_{16} = 1.1389$ | $n_9 = 1.54869$ | $\nu_9 = 45.55$ |
| $r_{17} = \infty$ | | | |
| | $d_{17} = 0.2436$ | $n_{10} = 1.51633$ | $\nu_{10} = 64.15$ |
| $r_{18} = \infty$ | | | |
| $f_F = 4.823$, | $D_1 = 0.972$, | $D_2 = 1.2$ | |
| $f_I = 1.481$, | $f_n = -0.648$, | $f_p = 1.314$ | |

EMBODIMENT 2

| | | | |
|---|---|---|---|
| $f = 1.000$, | F/4.815, | $2\omega = 133°$ | |
| $IH = 0.9857$ | | | |
| $r_1 = \infty$ | | | |
| | $d_1 = 0.2987$ | $n_1 = 1.88300$ | $\nu_1 = 40.78$ |
| $r_2 = 0.4920$ | | | |
| | $d_2 = 0.2210$ | | |
| $r_3 = 30.2837$ | | | |
| | $d_3 = 0.2747$ | $n_2 = 1.84666$ | $\nu_2 = 23.78$ |
| $r_4 = -1.1561$ | | | |
| | $d_4 = 0.0597$ | | |
| $r_5 = \infty$ (stop) | | | |
| | $d_5 = 0.1016$ | | |
| $r_6 = -4.1194$ | | | |
| | $d_6 = 0.1792$ | $n_3 = 1.80518$ | $\nu_3 = 25.43$ |
| $r_7 = 2.1470$ | | | |
| | $d_7 = 0.4779$ | $n_4 = 1.51633$ | $\nu_4 = 64.15$ |
| $r_8 = -0.7172$ | | | |
| | $d_8 = 0.1135$ | | |
| $r_9 = -46.5690$ | | | |
| | $d_9 = 0.1553$ | $n_5 = 1.84666$ | $\nu_5 = 23.78$ |
| $r_{10} = 1.2640$ | | | |
| | $d_{10} = 0.7168$ | $n_6 = 1.51633$ | $\nu_6 = 64.15$ |
| $r_{11} = -1.7141$ | | | |
| | $d_{11} = 0.1254$ | | |
| $r_{12} = \infty$ | | | |
| | $d_{12} = 0.2389$ | $n_7 = 1.51633$ | $\nu_7 = 64.15$ |
| $r_{13} = \infty$ | | | |
| | $d_{13} = 0.4182$ | $n_8 = 1.52000$ | $\nu_8 = 74.00$ |
| $r_{14} = \infty$ | | | |
| | $d_{14} = 0.2389$ | $n_9 = 1.51633$ | $\nu_9 = 64.15$ |
| $r_{15} = \infty$ | | | |
| | $d_{15} = 0.0896$ | | |
| $r_{16} = 2.3145$ | | | |
| | $d_{16} = 0.7168$ | $n_{10} = 1.53172$ | $\nu_{10} = 48.90$ |
| $r_{17} = -8.4075$ | | | |
| | $d_{17} = 0.6094$ | | |
| $r_{18} = \infty$ | | | |
| | $d_{18} = 1.1171$ | $n_{11} = 1.54869$ | $\nu_{11} = 45.55$ |
| $r_{19} = \infty$ | | | |
| | $d_{19} = 0.2389$ | $n_{12} = 1.51633$ | $\nu_{12} = 64.15$ |
| $r_{20} = \infty$ | | | |
| $f_F = 3.494$, | $D_1 = 0.805$, | $D_2 = 1.488$ | |
| $f_I = 1.954$, | $f_n = -0.557$, | $f_p = 1.18$ | |

EMBODIMENT 3

| | | | |
|---|---|---|---|
| $f = 1.000$, | F/5.884, | $2\omega = 96.902°$ | |
| $IH = 0.8238$ | | | |
| $r_1 = \infty$ | | | |
| | $d_1 = 0.2496$ | $n_1 = 1.88300$ | $\nu_1 = 40.78$ |
| $r_2 = 1.1373$ | | | |
| | $d_2 = 0.3145$ | | |
| $r_3 = \infty$ | | | |
| | $d_3 = 2.5062$ | $n_2 = 1.80610$ | $\nu_2 = 40.95$ |
| $r_4 = \infty$ (stop) | | | |
| | $d_4 = 0.0999$ | | |
| $r_5 = 2.2247$ | | | |
| | $d_5 = 0.3645$ | $n_3 = 1.72916$ | $\nu_3 = 54.68$ |
| $r_6 = -2.2247$ | | | |
| | $d_6 = 0.0999$ | | |
| $r_7 = \infty$ | | | |
| | $d_7 = 0.7489$ | $n_4 = 1.52000$ | $\nu_4 = 74.00$ |
| $r_8 = \infty$ | | | |
| | $d_8 = 0.6990$ | | |
| $r_9 = \infty$ | | | |
| | $d_9 = 0.6490$ | $n_5 = 1.51633$ | $\nu_5 = 64.15$ |
| $r_{10} = -0.8562$ | | | |
| | $d_{10} = 0.2496$ | $n_6 = 1.84666$ | $\nu_6 = 23.78$ |
| $r_{11} = -2.2676$ | | | |
| | $d_{11} = 0.2496$ | | |
| $r_{12} = 2.4094$ | | | |
| | $d_{12} = 0.5392$ | $n_7 = 1.72916$ | $\nu_7 = 54.68$ |
| $r_{13} = \infty$ | | | |
| | $d_{13} = 0.7489$ | $n_8 = 1.54869$ | $\nu_8 = 45.55$ |
| $r_{14} = \infty$ | | | |
| | $d_{14} = 0.1997$ | $n_9 = 1.51633$ | $\nu_9 = 64.15$ |
| $r_{15} = \infty$ | | | |
| $f_F = 3.078$, | $D_1 = 1.2916$, | $D_2 = 0.927$ | |
| $f_I = 1.257$, | $f_n = -1.288$, | $f_p = 1.58$ | |

EMBODIMENT 4

| | | | |
|---|---|---|---|
| $f = 1.000$, | F/4.984, | $2\omega = 113°$ | |
| $IH = 0.9242$ | | | |

-continued

| | | |
|---|---|---|
| $r_1 = \infty$ | | |
| | $d_1 = 0.2801$ | $n_1 = 1.88300 \quad \nu_1 = 40.78$ |
| $r_2 = 0.6120$ | | |
| | $d_2 = 0.3221$ | |
| $r_3 = 22.2335$ | | |
| | $d_3 = 0.3269$ | $n_2 = 1.76182 \quad \nu_2 = 26.55$ |
| $r_4 = -1.1753$ | | |
| | $d_4 = 0.1947$ | |
| $r_5 = \infty$ (stop) | | |
| | $d_5 = 0.2880$ | |
| $r_6 = -2.6427$ | | |
| | $d_6 = 0.2739$ | $n_3 = 1.72916 \quad \nu_3 = 54.68$ |
| $r_7 = -1.0365$ | | |
| | $d_7 = 0.0884$ | |
| $r_8 = \infty$ | | |
| | $d_8 = 0.8403$ | $n_4 = 1.52000 \quad \nu_4 = 74.00$ |
| $r_9 = \infty$ | | |
| | $d_9 = 0.1120$ | |
| $r_{10} = 2.7229$ | | |
| | $d_{10} = 0.7899$ | $n_5 = 1.51633 \quad \nu_5 = 64.15$ |
| $r_{11} = -0.9884$ | | |
| | $d_{11} = 0.2196$ | $n_6 = 1.84666 \quad \nu_6 = 23.78$ |
| $r_{12} = -4.9509$ | | |
| | $d_{12} = 0.2522$ | |
| $r_{13} = 2.4923$ | | |
| | $d_{13} = 0.4482$ | $n_7 = 1.88300 \quad \nu_7 = 40.78$ |
| $r_{14} = \infty$ | | |
| | $d_{14} = 0.8403$ | $n_8 = 1.54814 \quad \nu_8 = 45.78$ |
| $r_{15} = \infty$ | | |
| | $d_{15} = 0.2241$ | $n_9 = 1.51633 \quad \nu_9 = 64.15$ |
| $r_{16} = \infty$ | | |

$f_F = 2.741, \quad D_1 = 0.753, \quad D_2 = 0.928$
$f_I = 1.651, \quad f_n = -0.693, \quad f_p = 1.101$

EMBODIMENT 5

$f = 1.000, \quad F/5.099, \quad 2\omega = 113.58°$
$IH = 0.9693$

| | | |
|---|---|---|
| $r_1 = \infty$ | | |
| | $d_1 = 0.2938$ | $n_1 = 1.88300 \quad \nu_1 = 40.78$ |
| $r_2 = 0.5752$ | | |
| | $d_2 = 0.3779$ | |
| $r_3 = 3.6466$ | | |
| | $d_3 = 0.4113$ | $n_2 = 1.76182 \quad \nu_2 = 26.55$ |
| $r_4 = -0.6895$ | | |
| | $d_4 = 0.1763$ | $n_3 = 1.60729 \quad \nu_3 = 49.19$ |
| $r_5 = -1.7504$ | | |
| | $d_5 = 0.0588$ | |
| $r_6 = \infty$ (stop) | | |
| | $d_6 = 0.0588$ | |
| $r_7 = -4.2368$ | | |
| | $d_7 = 0.2644$ | $n_4 = 1.72916 \quad \nu_4 = 54.68$ |
| $r_8 = -1.2170$ | | |
| | $d_8 = 0.0588$ | |
| $r_9 = \infty$ | | |
| | $d_9 = 0.4700$ | $n_5 = 1.51633 \quad \nu_5 = 64.15$ |
| $r_{10} = \infty$ | | |
| | $d_{10} = 0.4113$ | $n_6 = 1.52000 \quad \nu_6 = 74.00$ |
| $r_{11} = \infty$ | | |
| | $d_{11} = 0.0588$ | |
| $r_{12} = 10.2100$ | | |
| | $d_{12} = 0.2627$ | $n_7 = 1.84666 \quad \nu_7 = 23.78$ |
| $r_{13} = 1.0151$ | | |
| | $d_{13} = 0.8813$ | $n_8 = 1.51633 \quad \nu_8 = 64.15$ |
| $r_{14} = -2.7301$ | | |
| | $d_{14} = 0.2563$ | |
| $r_{15} = 2.4108$ | | |
| | $d_{15} = 0.4700$ | $n_9 = 1.88300 \quad \nu_9 = 40.78$ |
| $r_{16} = \infty$ | | |
| | $d_{16} = 0.9988$ | $n_{10} = 1.54814 \quad \nu_{10} = 45.78$ |
| $r_{17} = \infty$ | | |
| | $d_{17} = 0.2350$ | $n_{11} = 1.51633 \quad \nu_{11} = 64.15$ |
| $r_{18} = \infty$ | | |

$f_F = 2.567, \quad D_1 = 0.698, \quad D_2 = 1.05$
$F_I = 1.305, \quad f_n = -0.651, \quad f_p = 0.97$

EMBODIMENT 6

$f = 1.000, \quad F/5.392, \quad 2\omega = 114.19°$
$IH = 0.9170$

| | | |
|---|---|---|
| $r_1 = \infty$ | | |
| | $d_1 = 0.2501$ | $n_1 = 1.88300 \quad \nu_1 = 40.78$ |
| $r_2 = 0.7277$ | | |
| | $d_2 = 0.2339$ | |
| $r_3 = 4.3359$ | | |
| | $d_3 = 0.4153$ | $n_2 = 1.84666 \quad \nu_2 = 23.78$ |
| $r_4 = -1.4744$ | | |
| | $d_4 = 0.1366$ | |
| $r_5 = \infty$ (stop) | | |
| | $d_5 = 0.0362$ | |
| $r_6 = -0.9343$ | | |
| | $d_6 = 0.3474$ | $n_3 = 1.51633 \quad \nu_3 = 64.15$ |
| $r_7 = -0.4485$ | | |
| | $d_7 = 0.2293$ | $n_4 = 1.84666 \quad \nu_4 = 23.78$ |
| $r_8 = -0.7496$ | | |
| | $d_8 = 0.0556$ | |
| $r_9 = 9.6712$ | | |
| | $d_9 = 0.4725$ | $n_5 = 1.65830 \quad \nu_5 = 57.33$ |
| $r_{10} = -1.5915$ | | |
| | $d_{10} = 0.0556$ | |
| $r_{11} = \infty$ | | |
| | $d_{11} = 0.3891$ | $n_6 = 1.52000 \quad \nu_6 = 74.00$ |
| $r_{12} = \infty$ | | |
| | $d_{12} = 0.3335$ | $n_7 = 1.51633 \quad \nu_7 = 64.15$ |
| $r_{13} = \infty$ | | |
| | $d_{13} = 0.4169$ | |
| $r_{14} = -1.0070$ | | |
| | $d_{14} = 0.2628$ | $n_8 = 1.84666 \quad \nu_8 = 23.78$ |
| $r_{15} = -1.3897$ | | |
| | $d_{15} = 0.2501$ | |
| $r_{16} = 2.4619$ | | |
| | $d_{16} = 0.4558$ | $n_9 = 1.77250 \quad \nu_9 = 49.66$ |
| $r_{17} = \infty$ | | |
| | $d_{17} = 0.8338$ | $n_{10} = 1.54814 \quad \nu_{10} = 45.78$ |
| $r_{18} = \infty$ | | |
| | $d_{18} = 0.2223$ | $n_{11} = 1.51633 \quad \nu_{11} = 64.15$ |
| $r_{19} = \infty$ | | |

$f_F = 3.187, \quad D_1 = 1.375, \quad D_2 = 0.942$
$f_I = 1.011, \quad f_n = -0.824, \quad f_p = 1.097$
$f_{an} = -6.307, \quad f_{ap}/f_{an} = -0.505, \quad f_{ap} = 3.185$

EMBODIMENT 7

$f = 1.000, \quad F/4.731, \quad 2\omega = 91.87°$
$IH = 0.9779$

| | | |
|---|---|---|
| $r_1 = \infty$ | | |
| | $d_1 = 0.2964$ | $n_1 = 1.88300 \quad \nu_1 = 40.78$ |
| $r_2 = 0.5733$ | | |
| | $d_2 = 0.2359$ | |
| $r_3 = -8.1777$ | | |
| | $d_3 = 0.4149$ | $n_2 = 1.76182 \quad \nu_2 = 26.55$ |
| $r_4 = -1.0023$ | | |
| | $d_4 = 0.0593$ | |
| $r_5 = \infty$ (stop) | | |
| | $d_5 = 0.6944$ | |
| $r_6 = -3.3322$ | | |
| | $d_6 = 0.2559$ | $n_3 = 1.72916 \quad \nu_3 = 54.68$ |
| $r_7 = -1.0387$ | | |
| | $d_7 = 0.0593$ | |
| $r_8 = \infty$ | | |
| | $d_8 = 0.2371$ | $n_4 = 1.51633 \quad \nu_4 = 64.15$ |
| $r_9 = \infty$ | | |
| | $d_9 = 0.0593$ | |
| $r_{10} = \infty$ | | |
| | $d_{10} = 0.4149$ | $n_5 = 1.52000 \quad \nu_5 = 74.00$ |
| $r_{11} = \infty$ | | |
| | $d_{11} = 0.0593$ | |
| $r_{12} = 3.3312$ | | |
| | $d_{12} = 0.8416$ | $n_6 = 1.51633 \quad \nu_6 = 64.15$ |
| $r_{13} = -0.9211$ | | |
| | $d_{13} = 0.2323$ | $n_7 = 1.84666 \quad \nu_7 = 23.78$ |
| $r_{14} = -6.2157$ | | |
| | $d_{14} = 0.2744$ | |
| $r_{15} = 2.7070$ | | |

-continued

|  |  |  |  |
|---|---|---|---|
| | $d_{15} = 0.4742$ | $n_8 = 1.88300$ | $\nu_8 = 40.78$ |
| $r_{16} = \infty$ | $d_{16} = 0.8892$ | $n_9 = 1.54814$ | $\nu_9 = 45.78$ |
| $r_{17} = \infty$ | $d_{17} = 0.2371$ | $n_{10} = 1.51633$ | $\nu_{10} = 64.15$ |
| $r_{18} = \infty$ | | | |
| $f_F = 3.065,$ | $D_1 = 0.607,$ | $D_2 = 0.783$ | |
| $f_I = 1.394,$ | $f_n = -0.649,$ | $f_p = 1.151$ | |
| $f_{an} = -22.063,$ | $f_{ap}/f_{an} = -0.139,$ | $f_{ap} = 3.067$ | |

EMBODIMENT 8

| $f = 1.000,$ | $F/4.890,$ | $2\omega = 113.60°$ |
|---|---|---|
| $IH = 0.9519$ | | |

|  |  |  |  |
|---|---|---|---|
| $r_1 = \infty$ | $d_1 = 0.2885$ | $n_1 = 1.88300$ | $\nu_1 = 40.78$ |
| $r_2 = 0.4627$ | $d_2 = 0.3789$ | | |
| $r_3 = -1.5369$ | $d_3 = 0.4039$ | $n_2 = 1.76182$ | $\nu_2 = 26.55$ |
| $r_4 = -0.6422$ | $d_4 = 0.0577$ | $n_3 = 1.60729$ | $\nu_3 = 49.19$ |
| $r_5 = -1.3542$ | $d_5 = 0.0577$ | | |
| $r_6 = \infty$ (stop) | $d_6 = 0.2308$ | | |
| $r_7 = -11.5530$ | $d_7 = 0.2597$ | $n_4 = 1.72916$ | $\nu_4 = 54.68$ |
| $r_8 = -1.0497$ | $d_8 = 0.0769$ | | |
| $r_9 = 6.3392$ | $d_9 = 0.2613$ | $n_5 = 1.51633$ | $\nu_5 = 64.15$ |
| $r_{10} = -3.2683$ | $d_{10} = 0.0577$ | | |
| $r_{11} = \infty$ | $d_{11} = 0.4616$ | $n_6 = 1.51633$ | $\nu_6 = 64.15$ |
| $r_{12} = \infty$ | $d_{12} = 0.4039$ | $n_7 = 1.52000$ | $\nu_7 = 74.00$ |
| $r_{13} = \infty$ | $d_{13} = 0.0577$ | | |
| $r_{14} = -18.4805$ | $d_{14} = 0.2580$ | $n_8 = 1.84666$ | $\nu_8 = 23.78$ |
| $r_{15} = 0.7943$ | $d_{15} = 0.8656$ | $n_9 = 1.51633$ | $\nu_9 = 64.15$ |
| $r_{16} = 14.3791$ | $d_{16} = 0.4365$ | | |
| $r_{17} = 2.2630$ | $d_{17} = 0.4616$ | $n_{10} = 1.88300$ | $\nu_{10} = 40.78$ |
| $r_{18} = \infty$ | $d_{18} = 0.8656$ | $n_{11} = 1.54814$ | $\nu_{11} = 45.78$ |
| $r_{19} = \infty$ | | | |
| $f_F = 2.563,$ | $D_1 = 0.686,$ | $D_2 = 0.804$ | |
| $f_I = 0.698,$ | $f_n = -0.524,$ | $f_p = 0.901$ | |
| $f_{an} = -1.961,$ | $f_{ap}/f_{an} = -1.307,$ | $f_{ap} = 2.563$ | |

EMBODIMENT 9

| $f = 1.000,$ | $F/4.557,$ | $2\omega = 93.64°$ |
|---|---|---|
| $IH = 1.0171$ | | |

|  |  |  |  |
|---|---|---|---|
| $r_1 = \infty$ | $d_1 = 0.3083$ | $n_1 = 1.88300$ | $\nu_1 = 40.78$ |
| $r_2 = 0.4949$ | $d_2 = 0.2401$ | | |
| $r_3 = -3.9191$ | $d_3 = 0.4316$ | $n_2 = 1.76182$ | $\nu_2 = 26.55$ |
| $r_4 = -0.8797$ | $d_4 = 0.0617$ | | |
| $r_5 = \infty$ (stop) | $d_5 = 0.2279$ | | |
| $r_6 = 3.6532$ | $d_6 = 0.1233$ | $n_3 = 1.84666$ | $\nu_3 = 23.78$ |
| $r_7 = 1.2519$ | $d_7 = 0.5584$ | $n_4 = 1.51633$ | $\nu_4 = 64.15$ |
| $r_8 = -0.8993$ | $d_8 = 0.0617$ | | |

-continued

|  |  |  |  |
|---|---|---|---|
| $r_9 = \infty$ | $d_9 = 0.2466$ | $n_5 = 1.51633$ | $\nu_5 = 64.15$ |
| $r_{10} = \infty$ | $d_{10} = 0.4316$ | $n_6 = 1.52000$ | $\nu_6 = 74.00$ |
| $r_{11} = \infty$ | $d_{11} = 0.1467$ | | |
| $r_{12} = 3.8777$ | $d_{12} = 0.2757$ | $n_7 = 1.84666$ | $\nu_7 = 23.78$ |
| $r_{13} = 0.9114$ | $d_{13} = 0.9248$ | $n_8 = 1.51633$ | $\nu_8 = 64.15$ |
| $r_{14} = -13.0363$ | $d_{14} = 0.2774$ | | |
| $r_{15} = 2.5448$ | $d_{15} = 0.4932$ | $n_9 = 1.88300$ | $\nu_9 = 40.78$ |
| $r_{16} = \infty$ | $d_{16} = 0.9248$ | $n_{10} = 1.54814$ | $\nu_{10} = 45.78$ |
| $r_{17} = \infty$ | $d_{17} = 0.2466$ | $n_{11} = 1.51633$ | $\nu_{11} = 64.15$ |
| $r_{18} = \infty$ | | | |
| $f_F = 2.883,$ | $D_1 = 0.655,$ | $D_2 = 1.022$ | |
| $f_I = 1.227,$ | $f_n = -0.561,$ | $f_p = 0.999$ | |
| $f_{an} = -11.02,$ | $f_{ap}/f_{an} = -0.262,$ | $f_{ap} = 2.887$ | |

EMBODIMENT 10

| $f = 1.000,$ | $F/4.877,$ | $2\omega = 115.07°$ |
|---|---|---|
| $IH = 0.9121$ | | |

|  |  |  |  |
|---|---|---|---|
| $r_1 = \infty$ | $d_1 = 0.2488$ | $n_1 = 1.88300$ | $\nu_1 = 40.78$ |
| $r_2 = 0.7435$ | $d_2 = 0.5417$ | | |
| $r_3 = 1.3809$ | $d_3 = 0.2764$ | $n_2 = 1.84666$ | $\nu_2 = 23.78$ |
| $r_4 = -1.3809$ | $d_4 = 0.0276$ | | |
| $r_5 = \infty$ (stop) | $d_5 = 0.0829$ | | |
| $r_6 = -0.8646$ | $d_6 = 0.1382$ | $n_3 = 1.84666$ | $\nu_3 = 23.78$ |
| $r_7 = 0.8646$ | $d_7 = 0.4809$ | $n_4 = 1.51633$ | $\nu_4 = 64.15$ |
| $r_8 = -0.8646$ | $d_8 = 0.0553$ | | |
| $r_9 = 47.8043$ | $d_9 = 0.4146$ | $n_5 = 1.69680$ | $\nu_5 = 55.52$ |
| $r_{10} = -1.2394$ | $d_{10} = 0.0553$ | | |
| $r_{11} = \infty$ | $d_{11} = 0.8292$ | $n_6 = 1.52000$ | $\nu_6 = 74.00$ |
| $r_{12} = \infty$ | $d_{12} = 0.2266$ | | |
| $r_{13} = -1.5777$ | $d_{13} = 0.1658$ | $n_7 = 1.84666$ | $\nu_7 = 23.78$ |
| $r_{14} = -5.2858$ | $d_{14} = 0.3206$ | $n_8 = 1.51633$ | $\nu_8 = 64.15$ |
| $r_{15} = -2.7855$ | $d_{15} = 0.2545$ | | |
| $r_{16} = 2.3306$ | $d_{16} = 0.4699$ | $n_9 = 1.77250$ | $\nu_9 = 49.66$ |
| $r_{17} = \infty$ | $d_{17} = 0.8292$ | $n_{10} = 1.54814$ | $\nu_{10} = 45.78$ |
| $r_{18} = \infty$ | $d_{18} = 0.2211$ | $n_{11} = 1.51633$ | $\nu_{11} = 64.15$ |
| $r_{19} = \infty$ | | | |
| $f_F = 3.018,$ | $D_1 = 0.828,$ | $D_2 = 0.946$ | |
| $f_I = 0.913,$ | $f_n = -0.842,$ | $f_p = 1.162$ | |
| $f_{an} = -3.871,$ | $f_{ap}/f_{an} = -0.780,$ | $f_{ap} = 3.019$ | |

EMBODIMENT 11

| $f = 1.000,$ | $F/5.000,$ | $2\omega = 85.12°$ |
|---|---|---|
| $IH = 0.8561$ | | |

|  |  |  |  |
|---|---|---|---|
| $r_1 = \infty$ | $d_1 = 0.2595$ | $n_1 = 1.88300$ | $\nu_1 = 40.78$ |
| $r_2 = 0.5514$ | $d_2 = 0.3444$ | | |

-continued

| | | | |
|---|---|---|---|
| $r_3 = 3.1680$ | | | |
| | $d_3 = 0.2595$ | $n_2 = 1.84666$ | $\nu_2 = 23.78$ |
| $r_4 = -3.7801$ | | | |
| | $d_4 = 0.1038$ | | |
| $r_5 = \infty$ (stop) | | | |
| | $d_5 = 0.1557$ | | |
| $r_6 = 2.8022$ | | | |
| | $d_6 = 0.1038$ | $n_3 = 1.84666$ | $\nu_3 = 23.78$ |
| $r_7 = 1.1582$ | | | |
| | $d_7 = 0.4152$ | $n_4 = 1.51633$ | $\nu_4 = 64.15$ |
| $r_8 = -0.9899$ | | | |
| | $d_8 = 0.0519$ | | |
| $r_9 = \infty$ | | | |
| | $d_9 = 0.3633$ | $n_5 = 1.51633$ | $\nu_5 = 64.15$ |
| $r_{10} = \infty$ | | | |
| | $d_{10} = 0.0519$ | | |
| $r_{11} = 2.9990$ | | | |
| | $d_{11} = 0.2595$ | $n_6 = 1.65830$ | $\nu_6 = 57.33$ |
| $r_{12} = -1.4480$ | | | |
| | $d_{12} = 0.0519$ | | |
| $r_{13} = \infty$ | | | |
| | $d_{13} = 0.2076$ | $n_7 = 1.51633$ | $\nu_7 = 64.15$ |
| $r_{14} = \infty$ | | | |
| | $d_{14} = 0.2617$ | | |
| $r_{15} = -0.8532$ | | | |
| | $d_{15} = 0.2076$ | $n_8 = 1.84666$ | $\nu_8 = 23.78$ |
| $r_{16} = -19.2311$ | | | |
| | $d_{16} = 0.3281$ | | |
| $r_{17} = 2.6607$ | | | |
| | $d_{17} = 0.4152$ | $n_9 = 1.77250$ | $\nu_9 = 49.66$ |
| $r_{18} = -3.2189$ | | | |
| | $d_{18} = 0.2076$ | | |
| $r_{19} = \infty$ | | | |
| | $d_{19} = 0.7784$ | $n_{10} = 1.54814$ | $\nu_{10} = 45.78$ |
| $r_{20} = \infty$ | | | |
| | $d_{20} = 0.2076$ | $n_{11} = 1.51633$ | $\nu_{11} = 64.15$ |
| $r_{21} = \infty$ | | | |
| $f_F = 1.946$, | $D_1 = 0.45$, | $D_2 = 0.847$ | |
| $f_I = 0.602$, | $f_n = -0.625$, | $f_p = 0.970$ | |
| $f_{an} = -1.060$, | $f_{ap}/f_{an} = -1.836$, | $f_{ap} = 1.946$ | |

EMBODIMENT 12

| | | | |
|---|---|---|---|
| $f = 1.000$, | $F/5.622$, | $2\omega = 100°$ | |
| $IH = 0.7937$ | | | |
| $r_1 = \infty$ | | | |
| | $d_1 = 0.2405$ | $n_1 = 1.88300$ | $\nu_1 = 40.78$ |
| $r_2 = 0.9296$ | | | |
| | $d_2 = 0.3367$ | | |
| $r_3 = \infty$ | | | |
| | $d_3 = 2.4146$ | $n_2 = 1.80610$ | $\nu_2 = 40.95$ |
| $r_4 = \infty$ (stop) | | | |
| | $d_4 = 0.0962$ | | |
| $r_5 = 2.3932$ | | | |
| | $d_5 = 0.4666$ | $n_3 = 1.78472$ | $\nu_3 = 25.71$ |
| $r_6 = -3.2917$ | | | |
| | $d_6 = 0.0481$ | | |
| $r_7 = 2.3396$ | | | |
| | $d_7 = 0.6494$ | $n_4 = 1.51633$ | $\nu_4 = 64.15$ |
| $r_8 = -0.8320$ | | | |
| | $d_8 = 0.2405$ | $n_5 = 1.84666$ | $\nu_5 = 23.78$ |
| $r_9 = -14.5825$ | | | |
| | $d_9 = 0.0962$ | | |
| $r_{10} = \infty$ | | | |
| | $d_{10} = 0.3752$ | $n_6 = 1.51633$ | $\nu_6 = 64.15$ |
| $r_{11} = -1.4667$ | | | |
| | $d_{11} = 0.0962$ | | |
| $r_{12} = \infty$ | | | |
| | $d_{12} = 0.7215$ | $n_7 = 1.51633$ | $\nu_7 = 64.15$ |
| $r_{13} = \infty$ | | | |
| | $d_{13} = 0.2453$ | | |
| $r_{14} = -1.0861$ | | | |
| | $d_{14} = 0.3848$ | $n_8 = 1.88300$ | $\nu_8 = 40.78$ |
| $r_{15} = -1.9685$ | | | |
| | $d_{15} = 0.1717$ | | |
| $r_{16} = 1.6004$ | | | |
| | $d_{16} = 0.5435$ | $n_9 = 1.51633$ | $\nu_9 = 64.15$ |
| $r_{17} = \infty$ | | | |
| | $d_{17} = 0.8995$ | $n_{10} = 1.54869$ | $\nu_{10} = 45.55$ |

-continued

| | | | |
|---|---|---|---|
| $r_{18} = \infty$ | | | |
| | $d_{18} = 0.1924$ | $n_{11} = 1.51633$ | $\nu_{11} = 64.15$ |
| $r_{19} = \infty$ | | | |
| $f_F = 3.099$, | $D_1 = 0.817$, | $D_2 = 1.066$ | |
| $f_I = 0.890$, | $f_n = -1.053$, | $f_p = 1.524$ | |
| $f_{an} = -4.196$, | $f_{ap}/f_{an} = -0.898$, | $f_{ap} = 3.768$ | |

EMBODIMENT 13

| | | | |
|---|---|---|---|
| $f = 1.000$ | $F/5.468$, | $2\omega = 57.02°$ | |
| $IH = 0.8287$ | | | |
| $r_1 = \infty$ | | | |
| | $d_1 = 0.2511$ | $n_1 = 1.88300$ | $\nu_1 = 40.78$ |
| $r_2 = 1.0415$ | | | |
| | $d_2 = 0.3516$ | | |
| $r_3 = \infty$ | | | |
| | $d_3 = 2.5213$ | $n_2 = 1.80610$ | $\nu_2 = 40.95$ |
| $r_4 = \infty$ (stop) | | | |
| | $d_4 = 0.1005$ | | |
| $r_5 = 3.2269$ | | | |
| | $d_5 = 0.2511$ | $n_3 = 1.51454$ | $\nu_3 = 54.69$ |
| $r_6 = -1.9257$ | | | |
| | $d_6 = 0.0506$ | | |
| $r_7 = 2.8064$ | | | |
| | $d_7 = 0.3415$ | $n_4 = 1.51633$ | $\nu_4 = 64.15$ |
| $r_8 = -2.7808$ | | | |
| | $d_8 = 0.1005$ | | |
| $r_9 = \infty$ | | | |
| | $d_9 = 0.7534$ | $n_5 = 1.51633$ | $\nu_5 = 64.15$ |
| $r_{10} = \infty$ | | | |
| | $d_{10} = 0.2562$ | | |
| $r_{11} = -3.4521$ | | | |
| | $d_{11} = 0.2511$ | $n_6 = 1.84666$ | $\nu_6 = 23.78$ |
| $r_{12} = 1.0907$ | | | |
| | $d_{12} = 0.6529$ | $n_7 = 1.51633$ | $\nu_7 = 64.15$ |
| $r_{13} = -2.0553$ | | | |
| | $d_{13} = 0.3813$ | | |
| $r_{14} = 1.6451$ | | | |
| | $d_{14} = 0.5676$ | $n_8 = 1.51633$ | $\nu_8 = 64.15$ |
| $r_{15} = \infty$ | | | |
| | $d_{15} = 0.7534$ | $n_9 = 1.54869$ | $\nu_9 = 45.55$ |
| $r_{16} = \infty$ | | | |
| | $d_{16} = 0.2009$ | $n_{10} = 1.51633$ | $\nu_{10} = 64.15$ |
| $r_{17} = \infty$ | | | |
| $f_F = 3.185$, | $D_1 = 0.854$, | $D_2 = 0.993$ | |
| $F_I = 0.829$, | $f_n = -1.179$, | $f_p = 1.339$ | |
| $f_{an} = -4.196$, | $f_{ap}/f_{an} = -0.759$, | $f_{ap} = 3.185$ | |

EMBODIMENT 14

| | | | |
|---|---|---|---|
| $f = 1.000$, | $F/3.950$, | $2\omega = 133.098°$ | |
| $IH = 1.0024$ | | | |
| $r_1 = \infty$ | | | |
| | $d_1 = 0.3038$ | $n_1 = 1.88300$ | $\nu_1 = 40.78$ |
| $r_2 = 0.5711$ | | | |
| | $d_2 = 0.2248$ | | |
| $r_3 = 2.9769$ | | | |
| | $d_3 = 0.3220$ | $n_2 = 1.84666$ | $\nu_2 = 83.78$ |
| $r_4 = -1.1896$ | | | |
| | $d_4 = 0.0608$ | | |
| $r_5 = \infty$ (stop) | | | |
| | $d_5 = 0.0608$ | | |
| $r_6 = -1.2284$ | | | |
| | $d_6 = 0.1823$ | $n_3 = 1.80518$ | $\nu_3 = 25.43$ |
| $r_7 = 1.6768$ | | | |
| | $d_7 = 0.6379$ | $n_4 = 1.51633$ | $\nu_4 = 64.15$ |
| $r_8 = -0.7874$ | | | |
| | $d_8 = 0.0608$ | | |
| $r_9 = 5.5207$ | | | |
| | $d_9 = 0.1580$ | $n_5 = 1.84666$ | $\nu_5 = 23.78$ |
| $r_{10} = 1.7339$ | | | |
| | $d_{10} = 0.8202$ | $n_6 = 1.51633$ | $\nu_6 = 64.15$ |
| $r_{11} = -1.7339$ | | | |
| | $d_{11} = 0.1276$ | | |
| $r_{12} = \infty$ | | | |
| | $d_{12} = 0.2430$ | $n_7 = 1.51633$ | $\nu_7 = 64.15$ |

-continued

| | | | |
|---|---|---|---|
| $r_{13} = \infty$ | | | |
| | $d_{13} = 0.4253$ | $n_8 = 1.52000$ | $\nu_8 = 74.00$ |
| $r_{14} = \infty$ | | | |
| | $d_{14} = 0.4192$ | | |
| $r_{15} = 2.2345$ | | | |
| | $d_{15} = 0.6987$ | $n_9 = 1.51603$ | $\nu_9 = 64.15$ |
| $r_{16} = 19.8755$ | | | |
| | $d_{16} = 0.0425$ | | |
| $r_{17} = \infty$ | | | |
| | $d_{17} = 0.2430$ | $n_{10} = 1.51633$ | $\nu_{10} = 64.15$ |
| $r_{18} = \infty$ | | | |
| | $d_{18} = 0.2430$ | | |
| $r_{19} = \infty$ | | | |
| | $d_{19} = 0.9118$ | $n_{11} = 1.54869$ | $\nu_{11} = 45.55$ |
| $r_{20} = \infty$ | | | |
| | $d_{20} = 0.2430$ | $n_{12} = 1.51633$ | $\nu_{12} = 64.15$ |
| $r_{21} = \infty$ | | | |
| $f_F = 4.811,$ | $D_1 = 0.9869,$ | $D_2 = 1.1944$ | |
| $f_I = 1.477,$ | $f_n = -0.647,$ | $f_p = 1.31$ | |

EMBODIMENT 15

| | | | |
|---|---|---|---|
| $f = 1.000,$ | $F/6.797,$ | $2\omega = 133.002°$ | |
| $IH = 0.9700$ | | | |
| $r_1 = \infty$ | | | |
| | $d_1 = 0.2939$ | $n_1 = 1.88300$ | $\nu_1 = 40.78$ |
| $r_2 = 0.5526$ | | | |
| | $d_2 = 0.2939$ | | |
| $r_3 = 10.5560$ | | | |
| | $d_3 = 0.2352$ | $n_2 = 1.84666$ | $\nu_2 = 23.78$ |
| $r_4 = -1.3550$ | | | |
| | $d_4 = 0.1451$ | | |
| $r_5 = \infty$ (stop) | | | |
| | $d_5 = 0.6146$ | | |
| $r_6 = -2.7945$ | | | |
| | $d_6 = 0.4590$ | $n_3 = 1.62280$ | $\nu_3 = 57.06$ |
| $r_7 = -1.1248$ | | | |
| | $d_7 = 0.0588$ | | |
| $r_8 = 10.0688$ | | | |
| | $d_8 = 0.8628$ | $n_4 = 1.51633$ | $\nu_4 = 64.15$ |
| $r_9 = -0.9345$ | | | |
| | $d_9 = 0.1293$ | $n_5 = 1.84666$ | $\nu_5 = 23.78$ |
| $r_{10} = -2.6316$ | | | |
| | $d_{10} = 0.1047$ | | |
| $r_{11} = 2.2906$ | | | |
| | $d_{11} = 0.6761$ | $n_6 = 1.69680$ | $\nu_6 = 55.52$ |
| $r_{12} = \infty$ | | | |
| | $d_{12} = 0.0176$ | | |
| $r_{13} = \infty$ | | | |
| | $d_{13} = 0.2352$ | $n_7 = 1.51633$ | $\nu_7 = 64.15$ |
| $r_{14} = \infty$ | | | |
| | $d_{14} = 0.0176$ | | |
| $r_{15} = \infty$ | | | |
| | $d_{15} = 0.6467$ | $n_8 = 1.52000$ | $\nu_8 = 74.00$ |
| $r_{16} = \infty$ | | | |
| | $d_{16} = 0.3527$ | | |
| $r_{17} = \infty$ | | | |
| | $d_{17} = 0.8818$ | $n_9 = 1.54869$ | $\nu_9 = 45.55$ |
| $r_{18} = \infty$ | | | |
| | $d_{18} = 0.2352$ | $n_{10} = 1.51633$ | $\nu_{10} = 64.15$ |
| $r_{19} = \infty$ | | | |
| $f_F = 3.287,$ | | $D_1 = 0.6146,$ | |
| $D_2 = 1.6930$ | | | |

EMBODIMENT 16

| | | | |
|---|---|---|---|
| $f = 1.000,$ | $F/3.723,$ | $2\omega = 133.584°$ | |
| $IH = 1.0523$ | | | |
| $r_1 \infty =$ | | | |
| | $d_1 = 0.3189$ | $n_1 = 1.88300$ | $\nu_1 = 40.78$ |
| $r_2\ 0.6107 =$ | | | |
| | $d_2 = 0.2360$ | | |
| $r_3\ 3.6012 =$ | | | |
| | $d_3 = 0.3380$ | $n_2 = 1.84666$ | $\nu_2 = 23.78$ |
| $r_4\ -1.1958 =$ | | | |
| | $d_4 = 0.0638$ | | |
| $r_5\ \infty$ (stop) $=$ | | | |
| | $d_5 = 0.0638$ | | |
| $r_6\ -1.2107 =$ | | | |
| | $d_6 = 0.1913$ | $n_3 = 1.80518$ | $\nu_3 = 25.43$ |
| $r_7 = 2.0604$ | | | |
| | $d_7 = 0.6696$ | $n_4 = 1.51633$ | $\nu_4 = 64.15$ |
| $r_8\ -0.8796 =$ | | | |
| | $d_8 = 0.0638$ | | |
| $r_9\ 6.1125 =$ | | | |
| | $d_9 = 0.1658$ | $n_5 = 1.84666$ | $\nu_5 = 23.78$ |
| $r_{10}\ 2.0098 =$ | | | |
| | $d_{10} = 0.8610$ | $n_6 = 1.51633$ | $\nu_6 = 64.15$ |
| $r_{11}\ -1.6842 =$ | | | |
| | $d_{11} = 0.1339$ | | |
| $r_{12}\ \infty =$ | | | |
| | $d_{12} = 0.2551$ | $n_7 = 1.51633$ | $\nu_7 = 64.15$ |
| $r_{13}\ \infty =$ | | | |
| | $d_{13} = 0.4464$ | $n_8 = 1.52000$ | $\nu_8 = 74.00$ |
| $r_{14}\ \infty =$ | | | |
| | $d_{14} = 0.2551$ | $n_9 = 1.51633$ | $\nu_9 = 64.15$ |
| $r_{15}\ \infty =$ | | | |
| | $d_{15} = 0.2572$ | | |
| $r_{16}\ 2.4259 =$ | | | |
| | $d_{16} = 0.7334$ | $n_{10} = 1.51633$ | $\nu_{10} = 64.15$ |
| $r_{17}\ -28.7961 =$ | | (aspherical surface) | |
| | $d_{17} = 0.3079$ | | |
| $r_{18}\ \infty =$ | | | |
| | $d_{18} = 1.1926$ | $n_{11} = 1.54869$ | $\nu_{11} = 45.55$ |
| $r_{19}\ \infty =$ | | | |
| | $d_{19} = 0.2551$ | $n_{12} = 1.51633$ | $\nu_{12} = 64.15$ |
| $r_{20}\ \infty =$ | | | | aspherical coefficient
$P = 1.0000,$  $E = 0.12395 \times 10^{-1}$
$F = 0.58165 \times 10^{-2}$
$f_F = 4.368,$  $D_1 = 1.0213,$  $D_2 = 1.2462$
$f_I = 1.549,$  $f_n = -0.692,$  $f_p = 1.404$

EMBODIMENT 17

| | | | |
|---|---|---|---|
| $f = 1.000,$ | $F/3.955,$ | $2\omega = 132.998°$ | |
| $IH = 1.0591$ | | | |
| $r_1\ \infty =$ | | | |
| | $d_1 = 0.3209$ | $n_1 = 1.88300$ | $\nu_1 = 40.78$ |
| $r_2\ 0.6509 =$ | | | |
| | $d_2 = 0.2375$ | | |
| $r_3\ 3.4933 =$ | | | |
| | $d_3 = 0.3402$ | $n_2 = 1.84666$ | $\nu_2 = 23.78$ |
| $r_4\ -1.2209 =$ | | | |
| | $d_4 = 0.0642$ | | |
| $r_5\ \infty$ (stop) $=$ | | | |
| | $d_5 = 0.0642$ | | |
| $r_6\ -1.0589 =$ | | | |
| | $d_6 = 0.1926$ | $n_3 = 1.80518$ | $\nu_3 = 25.43$ |

-continued

| | | |
|---|---|---|
| $r_7$ 1.8453 | | |
| $d_7 = 0.6739$ | $n_4 = 1.51633$ | $\nu_4 = 64.15$ |
| $r_8$ −0.8431 | | |
| $d_8 = 0.0642$ | | |
| $r_9$ 7.6048 | | |
| $d_9 = 0.1669$ | $n_5 = 1.84666$ | $\nu_5 = 23.78$ |
| $r_{10}$ 2.1084 | | |
| $d_{10} = 0.8665$ | $n_6 = 1.51633$ | $\nu_6 = 64.15$ |
| $r_{11}$ −1.5072 | | |
| $d_{11} = 0.1348$ | | |
| $r_{12}$ ∞ | | |
| $d_{12} = 0.2567$ | $n_7 = 1.51633$ | $\nu_7 = 64.15$ |
| $r_{13}$ ∞ | | |
| $d_{13} = 0.4493$ | $n_8 = 1.52000$ | $\nu_8 = 74.00$ |
| $r_{14}$ ∞ | | |
| $d_{14} = 0.2567$ | $n_9 = 1.51633$ | $\nu_9 = 64.15$ |
| $r_{15}$ ∞ | | |
| $d_{15} = 0.2710$ | | |
| $r_{16}$ 2.5636 | (aspherical surface) | |
| $d_{16} = 0.7381$ | $n_{10} = 1.51633$ | $\nu_{10} = 64.15$ |
| $r_{17}$ −117.1271 | | |
| $d_{17} = 0.3087$ | | |
| $r_{18}$ ∞ | | |
| $d_{18} = 1.2003$ | $n_{11} = 1.54869$ | $\nu_{11} = 45.55$ |
| $r_{19}$ ∞ | | |
| $d_{19} = 0.2567$ | $n_{12} = 1.51633$ | $\nu_{12} = 64.15$ |
| $r_{20}$ ∞ | | | aspherical coefficient
$P = 1.0000,$  $E = -0.81344 \times 10^{-2}$
$F = -0.46081 \times 10^{-2}$
$f_F = 4.869,$  $D_1 = 1.0400,$  $D_2 = 1.2530$
$f_I = 1.483,$  $f_n = -1.063,$  $f_p = 1.257$

EMBODIMENT 18

$f = 1.000,$  F/3.936,  $2\omega = 119.436°$
$IH = 1.0784$

| | | |
|---|---|---|
| $r_1$ 8.1850 | (aspherical surface) | |
| $d_1 = 0.3268$ | $n_1 = 1.88300$ | $\nu_1 = 40.78$ |
| $r_2$ 0.5640 | | |
| $d_2 = 0.2418$ | | |
| $r_3$ 3.1632 | | |
| $d_3 = 0.3464$ | $n_2 = 1.84666$ | $\nu_2 = 23.78$ |
| $r_4$ −1.2492 | | |
| $d_4 = 0.0654$ | | |
| $r_5$ ∞ (stop) | | |
| $d_5 = 0.0654$ | | |
| $r_6$ −1.1727 | | |
| $d_6 = 0.1961$ | $n_3 = 1.80518$ | $\nu_3 = 25.43$ |
| $r_7$ 1.9701 | | |
| $d_7 = 0.6863$ | $n_4 = 1.51633$ | $\nu_4 = 64.15$ |
| $r_8$ −0.8505 | | |
| $d_8 = 0.0654$ | | |
| $r_9$ 6.8599 | | |
| $d_9 = 0.1669$ | $n_5 = 1.84666$ | $\nu_5 = 23.78$ |

-continued

| | | |
|---|---|---|
| $r_{10}$ 1.9087 | | |
| $d_{10} = 0.8824$ | $n_6 = 1.51633$ | $\nu_6 = 64.15$ |
| $r_{11}$ −1.6859 | | |
| $d_{11} = 0.1373$ | | |
| $r_{12}$ ∞ | | |
| $d_{12} = 0.2614$ | $n_7 = 1.51633$ | $\nu_7 = 64.15$ |
| $r_{13}$ ∞ | | |
| $d_{13} = 0.4575$ | $n_8 = 1.52000$ | $\nu_8 = 74.00$ |
| $r_{14}$ ∞ | | |
| $d_{14} = 0.2614$ | $n_9 = 1.51633$ | $\nu_9 = 64.15$ |
| $r_{15}$ ∞ | | |
| $d_{15} = 0.2553$ | | |
| $r_{16}$ 2.3680 | | |
| $d_{16} = 0.7516$ | $n_{10} = 1.51633$ | $\nu_{10} = 64.15$ |
| $r_{17}$ −23.8332 | (aspherical surface) | |
| $d_{17} = 0.3154$ | | |
| $r_{18}$ ∞ | | |
| $d_{18} = 1.2222$ | $n_{11} = 1.54869$ | $\nu_{11} = 45.55$ |
| $r_{19}$ ∞ | | |
| $d_{19} = 0.2614$ | $n_{12} = 1.51633$ | $\nu_{12} = 64.15$ |
| $r_{20}$ ∞ | | | aspherical coefficient
(1st surface)
$P = 1.0000,$  $E = 0.27250 \times 10^{-1}$
$F = 0.38296 \times 10^{-2},$  $G = -0.74369 \times 10^{-2}$
(17th surface)
$P = 1.0000,$  $E = 0.25928 \times 10^{-1}$
$F = 0.32364 \times 10^{-2},$  $G = -0.83863 \times 10^{-4}$
$f_F = 4.213,$  $D_1 = 1.0384,$  $D_2 = 1.2770$
$f_I = 1.605,$  $f_n = -0.7,$  $f_p = 1.446$

EMBODIMENT 19

$f = 1.000,$  F/3.821,  $2\omega = 119.978°$
$IH = 1.0949$

| | | |
|---|---|---|
| $r_1$ 7.7641 | | |
| $d_1 = 0.3318$ | $n_1 = 1.88300$ | $\nu_1 = 40.78$ |
| $r_2$ 0.5903 | | |
| $d_2 = 0.2455$ | | |
| $r_3$ 3.2669 | | |
| $d_3 = 0.3517$ | $n_2 = 1.84666$ | $\nu_2 = 23.78$ |
| $r_4$ −1.3331 | | |
| $d_4 = 0.0664$ | | |
| $r_5$ ∞ (stop) | | |
| $d_5 = 0.0664$ | | |
| $r_6$ −1.2398 | | |
| $d_6 = 0.1991$ | $n_3 = 1.80518$ | $\nu_3 = 25.43$ |
| $r_7$ 1.7384 | | |
| $d_7 = 0.6967$ | $n_4 = 1.51633$ | $\nu_4 = 64.15$ |
| $r_8$ −0.8023 | | |
| $d_8 = 0.0664$ | | |
| $r_9$ 7.1278 | | |
| $d_9 = 0.1725$ | $n_5 = 1.84666$ | $\nu_5 = 23.78$ |
| $r_{10}$ 1.7921 | | |
| $d_{10} = 0.8958$ | $n_6 = 1.51633$ | $\nu_6 = 64.15$ |
| $r_{11}$ −1.6209 | | |
| $d_{11} = 0.1393$ | | |

-continued

| | | |
|---|---|---|
| $r_{12}$ ∞ = | | |
| $d_{12} = 0.2654$ | $n_7 = 1.51633$ | $\nu_7 = 64.15$ |
| $r_{13}$ ∞ = | | |
| $d_{13} = 0.4645$ | $n_8 = 1.52000$ | $\nu_8 = 74.00$ |
| $r_{14}$ ∞ = | | |
| $d_{14} = 0.2654$ | $n_9 = 1.51633$ | $\nu_9 = 64.15$ |
| $r_{15}$ ∞ = | | |
| $d_{15} = 0.2554$ | | |
| $r_{16}$ 2.5348 = | (aspherical surface) | |
| $d_{16} = 0.6172$ | $n_{10} = 1.51633$ | $\nu_{10} = 64.15$ |
| $r_{17}$ −35.5610 = | | |
| $d_{17} = 0.2346$ | | |
| $r_{18}$ ∞ = | | |
| $d_{18} = 1.2409$ | $n_{11} = 1.54869$ | $\nu_{11} = 45.55$ |
| $r_{19}$ ∞ = | | |
| $d_{19} = 0.2654$ | $n_{12} = 1.51633$ | $\nu_{12} = 64.15$ |
| $r_{20}$ ∞ | | | aspherical coefficient
(1st surface)
P = 1.0000,    E = 0.27612 × 10⁻¹
F = −0.29431 × 10⁻²
(16th surface)
P = 1.0000,    E = −0.13990 × 10⁻¹
F = −0.37958 × 10⁻²
$f_F = 4.608$,    $D_1 = 1.0503$,    $D_2 = 1.2109$
$f_I = 1.461$,    $f_n = -0.740$,    $f_p = 1.445$

EMBODIMENT 20

| | | |
|---|---|---|
| $f = 1.000$, | F/4.847, | $2\omega = 97°$ |
| IH = 0.9810 | | |
| $r_1$ ∞ = | (aspherical surface) | |
| $d_1 = 0.2973$ | $n_1 = 1.88300$ | $\nu_1 = 40.78$ |
| $r_2$ 1.1731 = | | |
| $d_2 = 0.3746$ | | |
| $r_3$ ∞ = | | |
| $d_3 = 2.9845$ | $n_2 = 1.840610$ | $\nu_2 = 40.95$ |
| $r_4$ ∞ (stop) = | | |
| $d_4 = 0.1189$ | | |
| $r_5$ 2.4507 = | | |
| $d_5 = 0.4340$ | $n_3 = 1.72916$ | $\nu_3 = 54.68$ |
| $r_6$ −4.4018 = | | |
| $d_6 = 0.1189$ | | |
| $r_7$ ∞ = | | |
| $d_7 = 0.8918$ | $n_4 = 1.52000$ | $\nu_4 = 74.00$ |
| $r_8$ ∞ = | | |
| $d_8 = 0.8323$ | | |
| $r_9$ 3.1928 = | | |
| $d_9 = 0.7729$ | $n_5 = 1.51633$ | $\nu_5 = 64.15$ |
| $r_{10}$ −1.0249 = | | |
| $d_{10} = 0.2973$ | $n_6 = 1.84666$ | $\nu_6 = 23.78$ |
| $r_{11}$ −1.9712 = | | |
| $d_{11} = 0.3158$ | | |
| $r_{12}$ 4.2521 = | (aspherical surface) | |
| $d_{12} = 0.6421$ | $n_7 = 1.72916$ | $\nu_7 = 54.68$ |
| $r_{13}$ ∞ = | | |
| $d_{13} = 0.8918$ | $n_8 = 1.54869$ | $\nu_8 = 45.55$ |

-continued

| | | |
|---|---|---|
| $r_{14}$ ∞ = | | |
| $d_{14} = 0.2378$ | $n_9 = 1.51633$ | $\nu_9 = 64.15$ |
| $r_{15}$ ∞ | | | aspherical coefficient
(1st surface)
P = 1.0000,    E = 0.21885 × 10⁻¹,    B = 0.57318 × 10⁻¹
F = −0.34067 × 10⁻²
(12th surface)
P = −44.7174,    E = 0.26922 × 10⁻¹
F = −0.43239 × 10⁻¹,    G = 0.23067 × 10⁻¹
$f_F = 5.832$,    $D_1 = 1.538$,    $D_2 = 1.104$
$f_I = 2.325$,    $f_n = -1.564$,    $f_p = 2.218$

EMBODIMENT 21

| | | |
|---|---|---|
| $f = 1.000$, | F/3.635, | $2\omega = 113.602°$ |
| IH = 1.2017 | | |
| $r_1$ ∞ = | (aspherical surface) | |
| $d_1 = 0.3277$ | $n_1 = 1.80610$ | $\nu_1 = 40.95$ |
| $r_2$ 0.5828 = | | |
| $d_2 = 0.7138$ | | |
| $r_3$ −3.7267 = | | |
| $d_3 = 0.3642$ | $n_2 = 1.84666$ | $\nu_2 = 23.78$ |
| $r_4$ −1.2734 = | | |
| $d_4 = 0.0364$ | | |
| $r_5$ ∞ (stop) = | | |
| $d_5 = 0.1092$ | | |
| $r_6$ −1.8059 = | | |
| $d_6 = 0.1821$ | $n_3 = 1.84666$ | $\nu_3 = 23.78$ |
| $r_7$ 1.5570 = | | |
| $d_7 = 0.6336$ | $n_4 = 1.51633$ | $\nu_4 = 64.15$ |
| $r_8$ −1.2178 = | | |
| $d_8 = 0.0728$ | | |
| $r_9$ 6.2187 = | | |
| $d_9 = 0.5462$ | $n_5 = 1.69680$ | $\nu_5 = 55.52$ |
| $r_{10}$ −1.8999 = | | |
| $d_{10} = 0.0728$ | | |
| $r_{11}$ ∞ = | | |
| $d_{11} = 1.0925$ | $n_6 = 1.52000$ | $\nu_6 = 74.00$ |
| $r_{12}$ ∞ = | | |
| $d_{12} = 0.2986$ | | |
| $r_{13}$ −2.2076 = | | |
| $d_{13} = 0.2185$ | $n_7 = 1.84666$ | $\nu_7 = 23.78$ |
| $r_{14}$ 43.3086 = | | |
| $d_{14} = 0.4224$ | $n_8 = 1.51633$ | $\nu_8 = 64.15$ |
| $r_{15}$ −2.5432 = | | |
| $d_{15} = 0.3038$ | | |
| $r_{16}$ 2.3477 = | (aspherical surface) | |
| $d_{16} = 0.6191$ | $n_9 = 1.77250$ | $\nu_9 = 49.66$ |
| $r_{17}$ ∞ = | | |
| $d_{17} = 1.0925$ | $n_{10} = 1.54814$ | $\nu_{10} = 45.78$ |
| $r_{18}$ ∞ = | | |
| $d_{18} = 0.2913$ | $n_{11} = 1.51633$ | $\nu_{11} = 64.15$ |
| $r_{19}$ ∞ | | | aspherical coefficient
(1st surface)
P = 1.0000,    E = 0.19990,    B = 0.23517
F = −0.16297,    G = 0.43056 × 10⁻¹

-continued (16th surface)
P = −4.3010, E = −0.12093 × 10⁻¹
F = 0.66784 × 10⁻²
$f_F$ = 3.039, $D_1$ = 1.09, $D_2$ = 1.247
$f_I$ = 1.081, $f_n$ = −1.1, $f_p$ = 1.417
$f_{ap}/f_{an}$ = −0.477, $f_{an}$ = −6.365

EMBODIMENT 22 f = 1.000, F/3.826, 2ω = 120°
IH = 1.0963
$r_1$ 7.3216 (aspherical surface)
  $d_1$ = 0.3322   $n_1$ = 1.88300   $\nu_1$ = 40.78
$r_2$ 0.5839
  $d_2$ = 0.2458
$r_3$ 3.2317
  $d_3$ = 0.3522   $n_2$ = 1.84666   $\nu_2$ = 23.78
$r_4$ −1.3470
  $d_4$ = 0.0664
$r_5$ ∞ (stop)
  $d_5$ = 0.0664
$r_6$ −1.2449
  $d_6$ = 0.1993   $n_3$ = 1.80518   $\nu_3$ = 25.43
$r_7$ 1.6804
  $d_7$ = 0.6977   $n_4$ = 1.51633   $\nu_4$ = 64.15
$r_8$ −0.7957
  $d_8$ = 0.0664
$r_9$ 7.0988
  $d_9$ = 0.1728   $n_5$ = 1.84666   $\nu_5$ = 23.78
$r_{10}$ 1.7664
  $d_{10}$ = 0.8970   $n_6$ = 1.51633   $\nu_6$ = 64.15
$r_{11}$ −1.6196
  $d_{11}$ = 0.1395
$r_{12}$ ∞
  $d_{12}$ = 0.2658   $n_7$ = 1.51633   $\nu_7$ = 64.15
$r_{13}$ ∞
  $d_{13}$ = 0.4651   $n_8$ = 1.52000   $\nu_8$ = 74.00
$r_{14}$ ∞
  $d_{14}$ = 0.2658   $n_9$ = 1.51633   $\nu_9$ = 64.15
$r_{15}$ ∞
  $d_{15}$ = 0.2543
$r_{16}$ 2.5285 (aspherical surface)
  $d_{16}$ = 0.6264   $n_{10}$ = 1.51633   $\nu_{10}$ = 64.15
$r_{17}$ −54.0626 (aspherical surface)
  $d_{17}$ = 0.2414
$r_{18}$ ∞
  $d_{18}$ = 1.2425   $n_{11}$ = 1.54869   $\nu_{11}$ = 45.55
$r_{19}$ ∞
  $d_{19}$ = 0.2658   $n_{12}$ = 1.51633   $\nu_{12}$ = 64.15
$r_{20}$ ∞ aspherical coefficient
(1st surface)
P = 1.0000, E = 0.33020 × 10⁻¹
F = −0.78286 × 10⁻²
(16th surface)
P = 1.0000, E = −0.14437 × 10⁻¹
F = −0.24025 × 10⁻²
(17th surface)
P = 1.0000, E = 0.99295 × 10⁻³

F = −0.84124 × 10⁻³
$f_F$ = 4.696, $D_1$ = 1.0504, $D_2$ = 1.2190
$f_I$ = 1.458, $f_n$ = −0.736, $f_p$ = 1.447

EMBODIMENT 23 f = 1.000, F/4.031, 2ω = 120.55°
IH = 1.1371
$r_1$ 3.8935 (aspherical surface)
  $d_1$ = 0.3446   $n_1$ = 1.88300   $\nu_1$ = 40.78
$r_2$ 0.6525
  $d_2$ = 0.3170
$r_3$ −13.5877
  $d_3$ = 0.3653   $n_2$ = 1.84666   $\nu_2$ = 23.78
$r_4$ −1.5462
  $d_4$ = 0.0689
$r_5$ ∞ (stop)
  $d_5$ = 0.0689
$r_6$ −1.3756
  $d_6$ = 0.2068   $n_3$ = 1.80518   $\nu_3$ = 25.43
$r_7$ 2.5197
  $d_7$ = 0.7236   $n_4$ = 1.51633   $\nu_4$ = 64.15
$r_8$ −0.8700
  $d_8$ = 0.0689
$r_9$ 5.4855 (aspherical surface)
  $d_9$ = 0.1792   $n_5$ = 1.84666   $\nu_5$ = 23.78
$r_{10}$ 1.8708
  $d_{10}$ = 0.9304   $n_6$ = 1.51633   $\nu_6$ = 64.15
$r_{11}$ −1.7408
  $d_{11}$ = 0.1203
$r_{12}$ ∞
  $d_{12}$ = 0.2757   $n_7$ = 1.51633   $\nu_7$ = 64.15
$r_{13}$ ∞
  $d_{13}$ = 0.4824   $n_8$ = 1.52000   $\nu_8$ = 74.00
$r_{14}$ ∞
  $d_{14}$ = 0.2757   $n_9$ = 1.51633   $\nu_9$ = 64.15
$r_{15}$ ∞
  $d_{15}$ = 0.2117
$r_{16}$ 2.3721 (aspherical surface)
  $d_{16}$ = 0.8012   $n_{10}$ = 1.51633   $\nu_{10}$ = 64.15
$r_{17}$ 20.6589
  $d_{17}$ = 0.3086
$r_{18}$ ∞
  $d_{18}$ = 1.2888   $n_{11}$ = 1.54869   $\nu_{11}$ = 45.55
$r_{19}$ ∞
  $d_{19}$ = 0.2757   $n_{12}$ = 1.51633   $\nu_{12}$ = 64.15
$r_{20}$ ∞ aspherical coefficient
(1st surface)
P = 1.0000, E = 0.10301
F = −0.76500 × 10⁻¹, G = 0.12298 × 10⁻¹
(9th surface)
P = 1.0000, E = −0.14962 × 10⁻¹
F = −0.12839 × 10⁻¹
(16th surface)
P = 1.0000, E = −0.14686 × 10⁻¹
F = 0.10545 × 10⁻²
$f_F$ = 5.114, $D_1$ = 1.0130, $D_2$ = 1.3226

-continued

| $f_I = 1.532,$ | $f_n = -0.934,$ | $f_p = 1.581$ |
|---|---|---| wherein the reference symbols $r_1, r_2, \ldots$ represent radii of curvature on the surfaces of the respective lens elements, the reference symbols $d_1, d_2, \ldots$ designate thicknesses of the respective lens elements and airspaces reserved therebetween, the reference symbols $n_1, n_2, \ldots$ denote refractive indices of the respective lens elements, and the reference symbols $\nu_1, \nu_2, \ldots$ represent Abbe's numbers of the respective lens elements.

When the direction along the optical axis is taken as the x axis and the direction perpendicular to the optical axis is taken as the y axis, the shapes of the aspherical surfaces used in Embodiments 16 through 23 are expressed by the following formula:

$$y = \frac{\frac{x^2}{r}}{1+\sqrt{1-P\left(\frac{x}{r}\right)^2}} + Bx^2 + Ex^4 + Fx^6 + Gx^8 + \ldots$$

wherein the reference symbol r represents radius of curvature at the vertex of the aspherical surface, the reference symbols p designate the conic constant and the reference symbols $B,E,F,G,\ldots$ denote the coefficients of aspherical surface.

Figure 2:
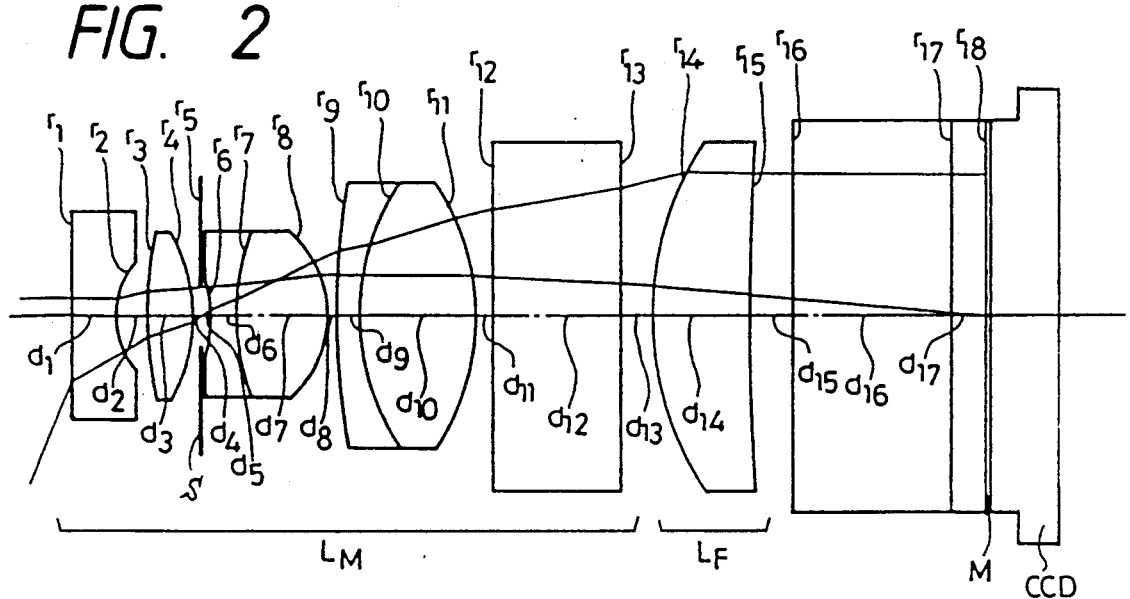
Figure 3:
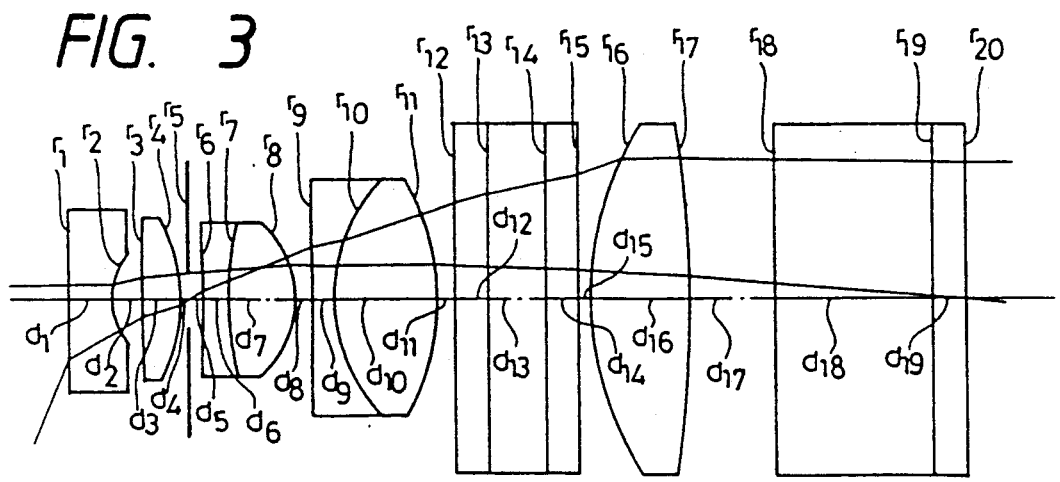
Figure 4:
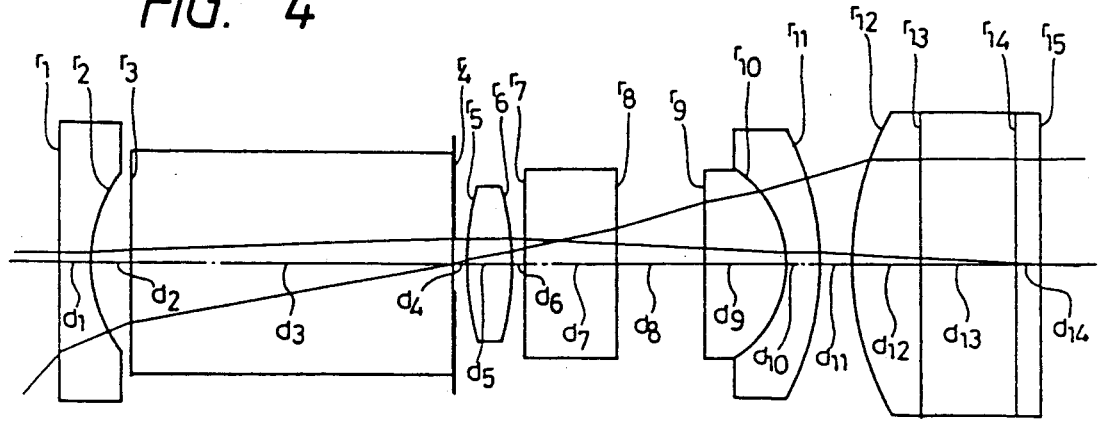
Figure 5:
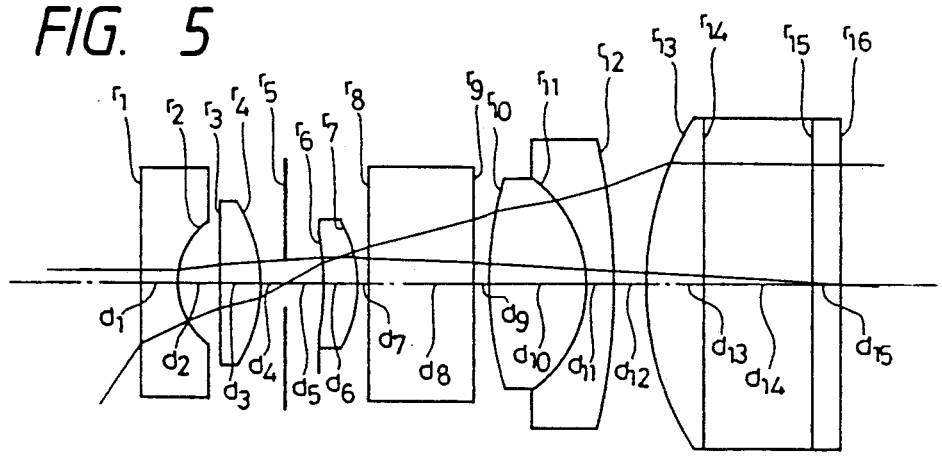
Figure 6:
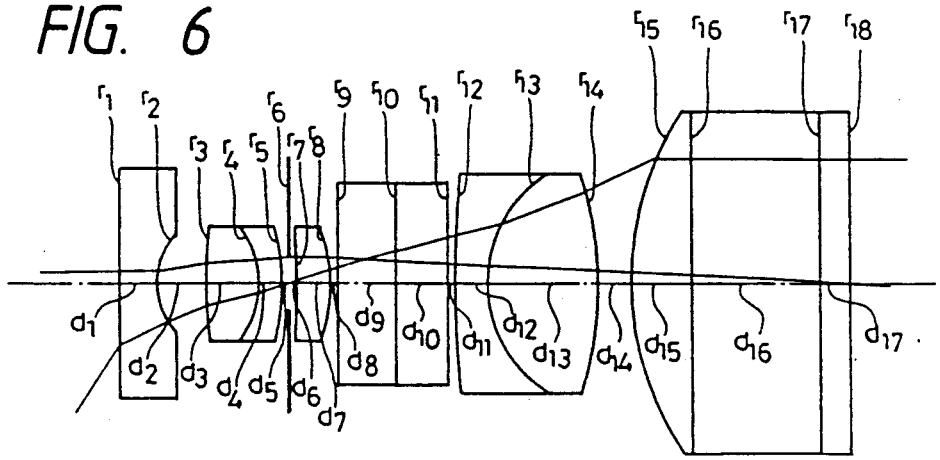
Figure 10:
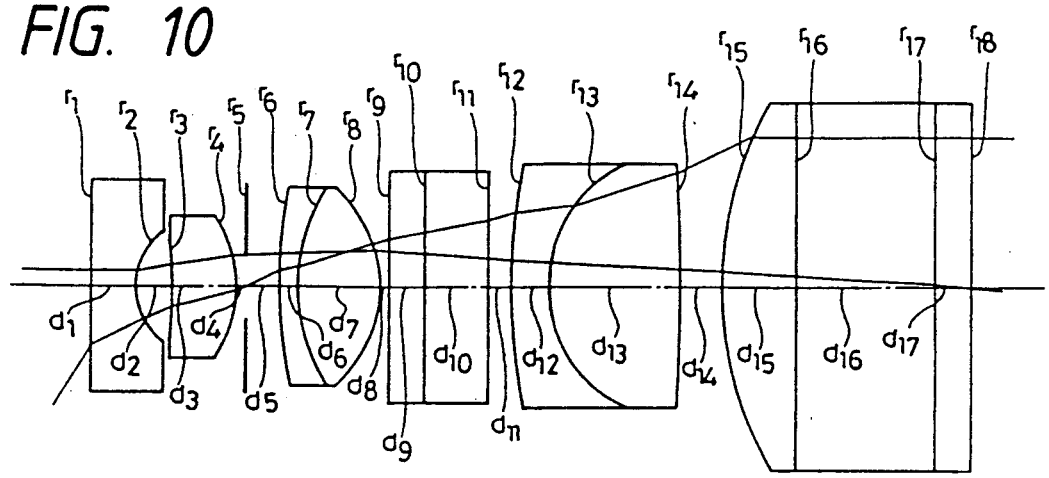
Figure 11:
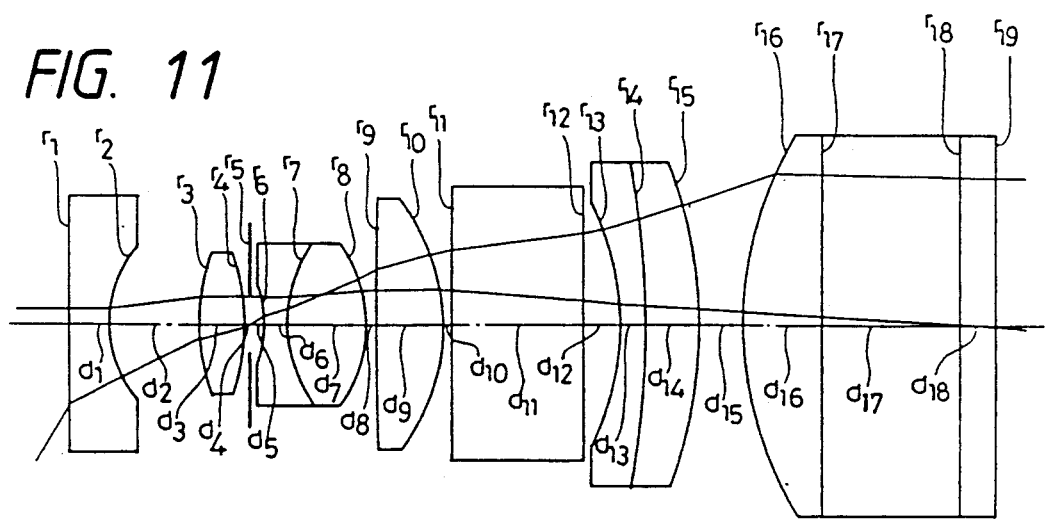
Figure 12:
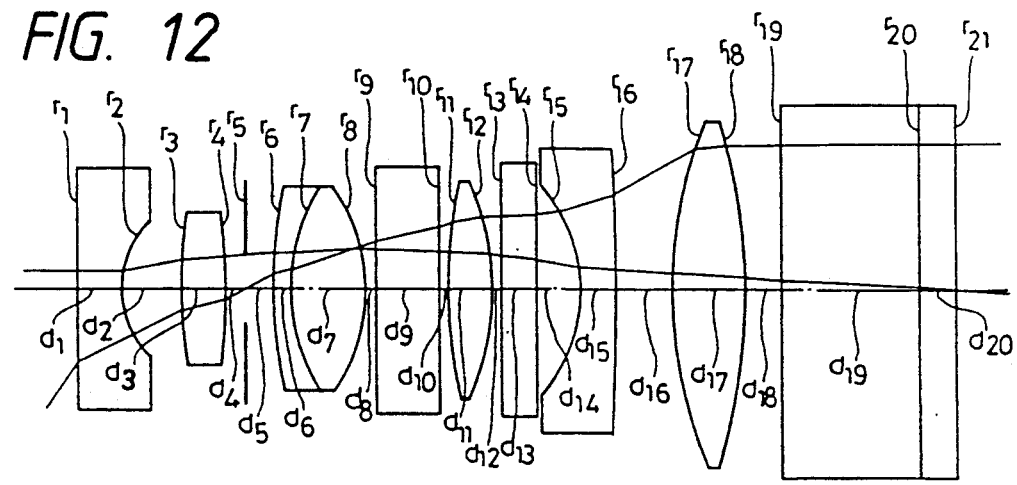
Figure 13:
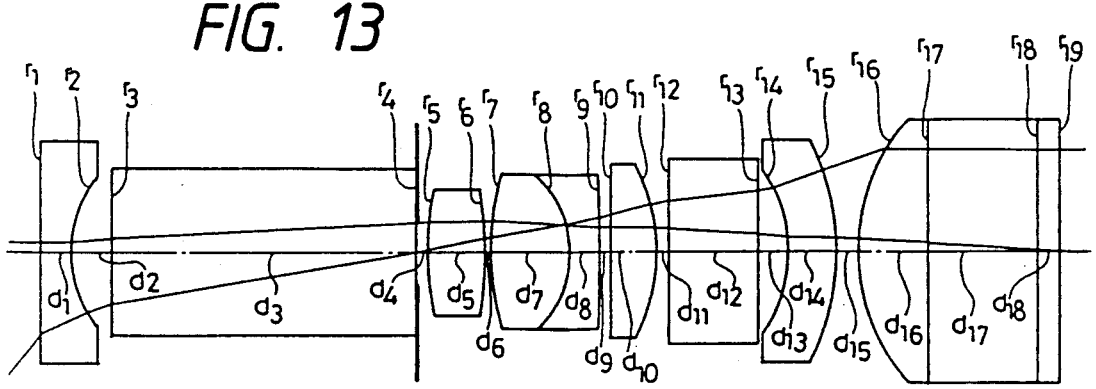
Figure 14:
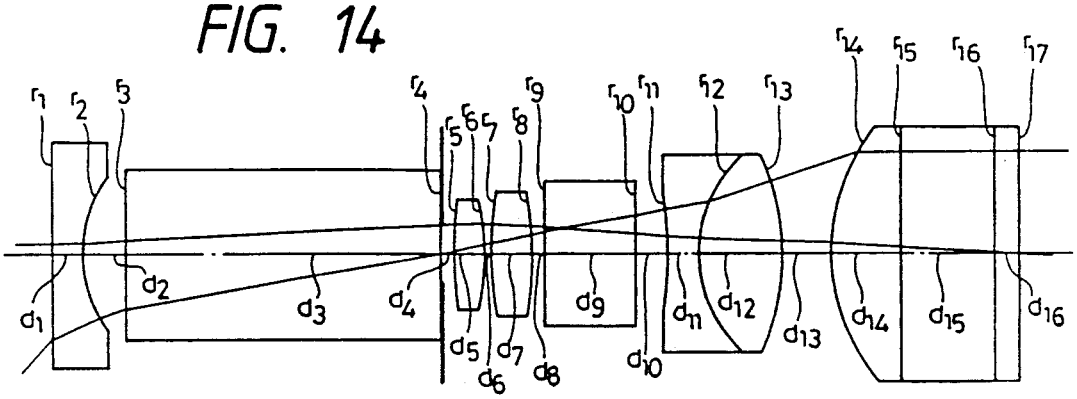

It is preferable for correcting coma and lateral chromatic aberration to arrange a positive lens component on the object side of the aperture stop as illustrated, for example, in FIG. 2 out of the drawings showing the Embodiments. When only negative lens components are arranged on the object side of the aperture stop, the optical system is asymmetrical. By arranging the positive lens component as described above, it is possible to moderate the asymmetry of the optical system, correct lower coma so as to be positive and obtain an advantage for correction of lateral chromatic aberration.

In the Embodiments 6 through 13, the rear subsystems comprise nearly afocal sections. The nearly afocal sections in the rear subsystems mean sections in which the principal ray is incident nearly in parallel with the optical axis and emerges nearly in parallel with the optical axis. In the Embodiment 6 (FIG. 7), for example, the principal ray is nearly in parallel (approximately 15°) with the optical axis between the lens component $L_A$ and the lens component $L_B$, and the principal ray is again in parallel with the optical axis after it emerges from the field lens component $L_F$. The nearly afocal optical system in the Embodiment 6 is the section composed of the lens component $L_B$ and the field lens component $L_F$.

The Embodiment 6, in which the principal ray has an inclination angle of 4° or smaller on the image surface and is nearly parallel with the optical axis, comprises a section in which the principal ray has an inclination angle of 18° or smaller, i.e., a nearly afocal section. When an interference filter such as an infrared cut filter is interposed in such an embodiment, color shading cannot be produced on the screen since angles of incidence of rays incident on the interference filter vary little.

Further, the Embodiments 6 through 13 are so designed as to satisfy the following condition (7):

$$f_{ap}/f_{an} < -0.1 \tag{7}$$

wherein the reference symbols $f_{ap}$ and $f_{an}$ represent focal lengths of the lens component having positive power and the lens component having negative power respectively in the nearly afocal optical section.

The condition (7) defines the value which is generally referred to as the afocal ratio. When this value becomes close to 0, the rays incident on the rear subsystem have larger angles of incidence, and angles of incidence are larger on the filter arranged between the front subsystem and the rear subsystem. Accordingly, it is permissible to arrange a filter whose characteristic is easily changed depending on variation of angles of incidence. It is desirable for the above-mentioned afocal ratio to have a large absolute value since such a value lowers heights of rays incident on the rear subsystem, thereby making it possible to reduce diameter of the optical system. When the afocal ratio has a value closer to 0 than $-0.1$, however, the optical system has a large diameter and cannot be set in the distal ends of endoscopes.

Further, it is desirable to design the optical system for endoscopes according to the present invention so as to satisfy the following condition (8):

$$-40f < f_{an} < -0.2f \tag{8}$$

When $|f_{an}|$ becomes larger while keeping the rear subsystem kept in the nearly afocal condition, the optical system tends to have a longer total length. If $f_{an}$ is smaller than $-40f$, it will be impossible to set an objective lens system in the distal ends of endoscopes. If the negative lens component arranged in the afocal optical system has too strong power and makes $f_{an}$ larger than $-0.2f$, on the other hand, it will be difficult to correct aberrations.

In the Embodiments 1 and 2 wherein the field lens component $L_F$ is not integrated with an image pickup device, angle of incidence of the principal ray incident on the image pickup device is not changed and field angle is varied little by adjusting the airspace between the optical system and the image pickup device for locating the image pickup device at predetermined position at the assembly stage.

The Embodiments 3, 4 and 5 wherein the field lens component $L_F$ is integrated with an image pickup device enable to shorten total length of the optical system.

The Embodiments 3, 12 and 13 are optical systems usable also for side viewing or oblique viewing. For such a purpose, it is sufficient to use a field direction changing prism such as a roof prism in place of the plane parallel plate arranged on the object side of the aperture stop. Out of these Embodiments, the Embodiments 12 and 13 are optical systems comprising nearly afocal sections in the rear subsystems thereof.

The Embodiment 6 is a forward viewing optical system wherein the rear subsystem is designed as a nearly afocal optical system.

The Embodiment 7 is an optical system comprising a smaller number of lens elements and so adapted as to reserve a wider airspace between the aperture stop and the convex lens component arranged on the image side thereof so that the rays are nearly in parallel with the optical axis.

In the Embodiment 8, the convex lens component arranged on the object side of the aperture stop is designed as a cemented doublet for correcting lateral chromatic aberration.

In the Embodiment 9, the convex lens component arranged on the image side of the aperture stop is designed as a cemented doublet for correcting coma.

In the Embodiment 10, the concave lens component arranged in the rear subsystem is designed as a cemented doublet for enhancing workability of the concave lens component.

The Embodiment 11 is characterized in that the filter is divided into two, the object side filter is designed as an absorption filter and the image side filter is designed as an interference filter for shortening total length of the optical system, and that a focus adjusting space is reserved between the field lens component and the filter arranged on the image side thereof for minimizing variation of field angle to be caused by focusing.

Figure 15:
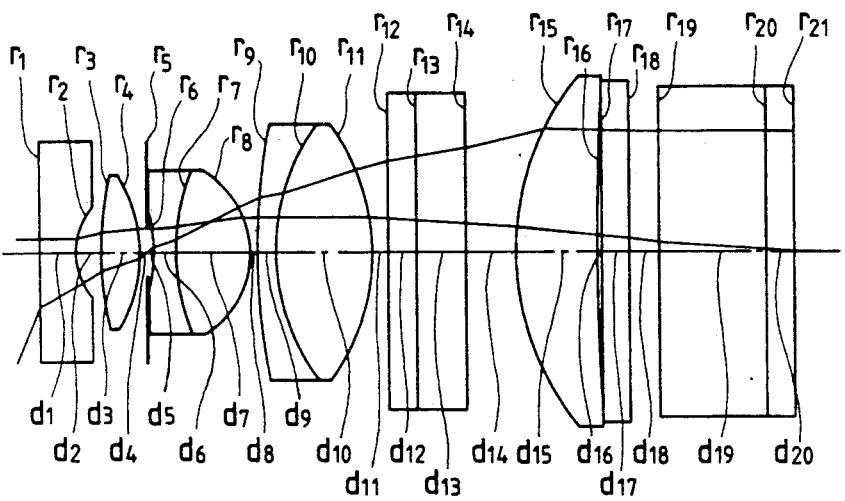
Figure 16:
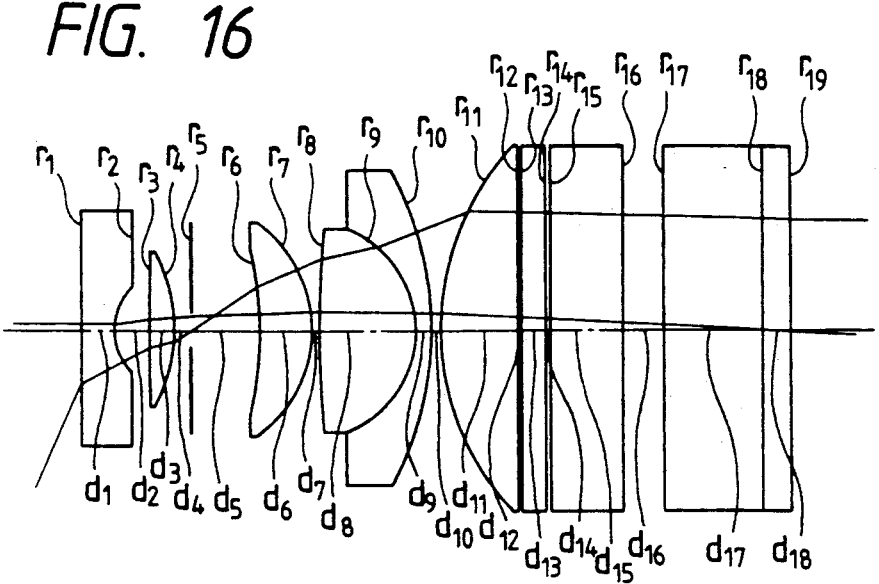
Figure 17:
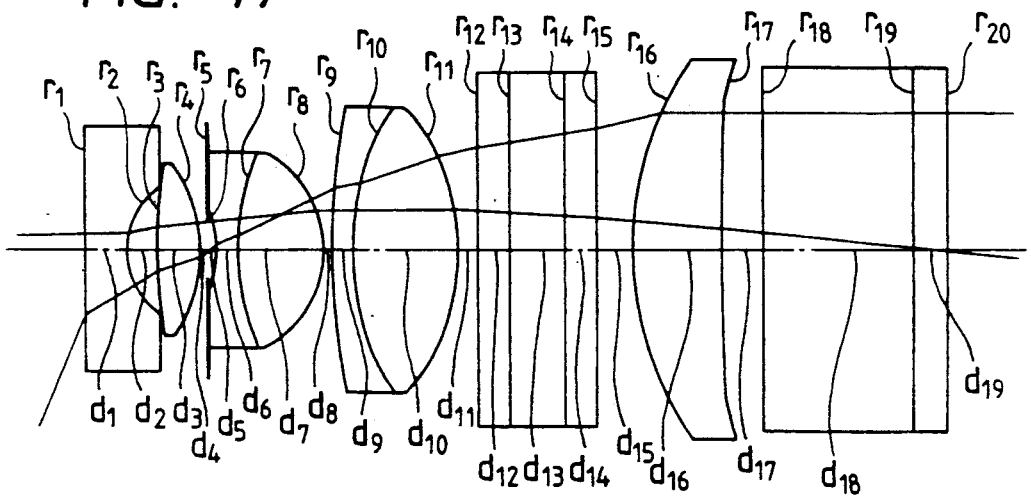
Figure 18:
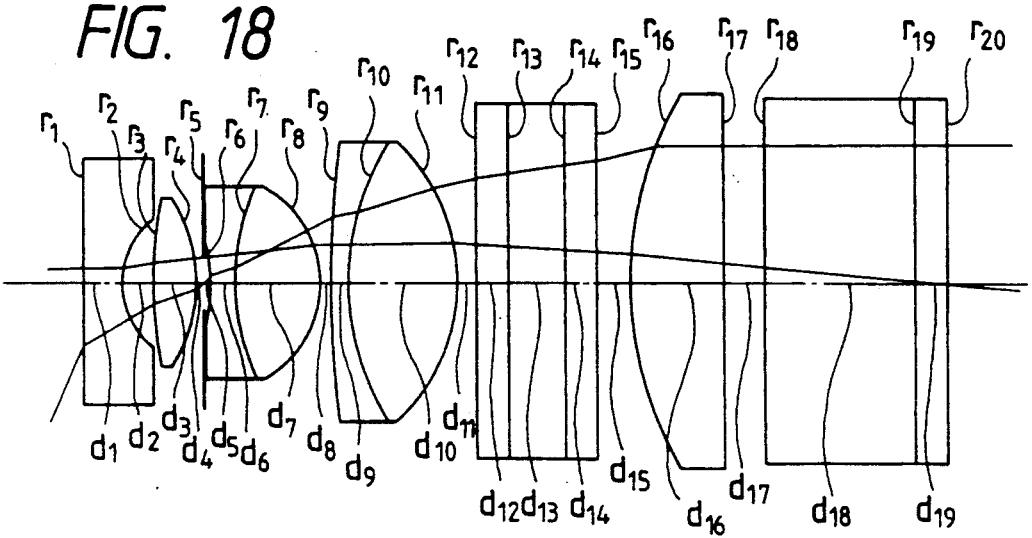
Figure 19:
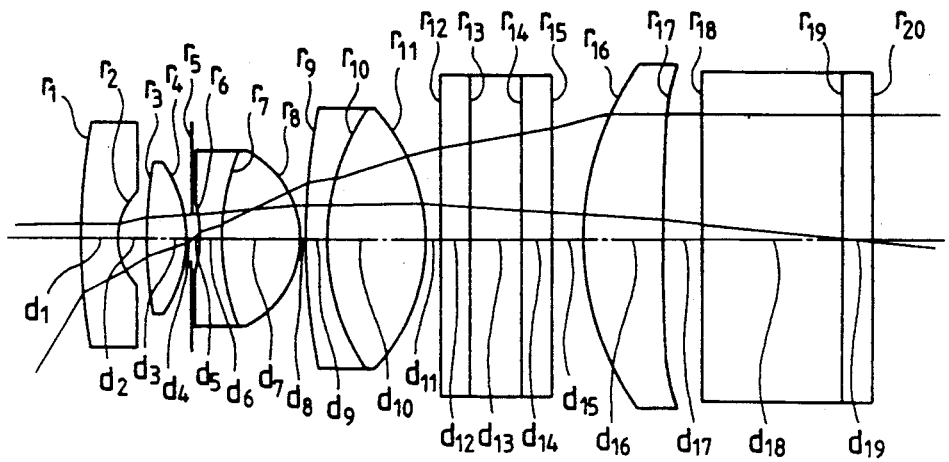
Figure 20:
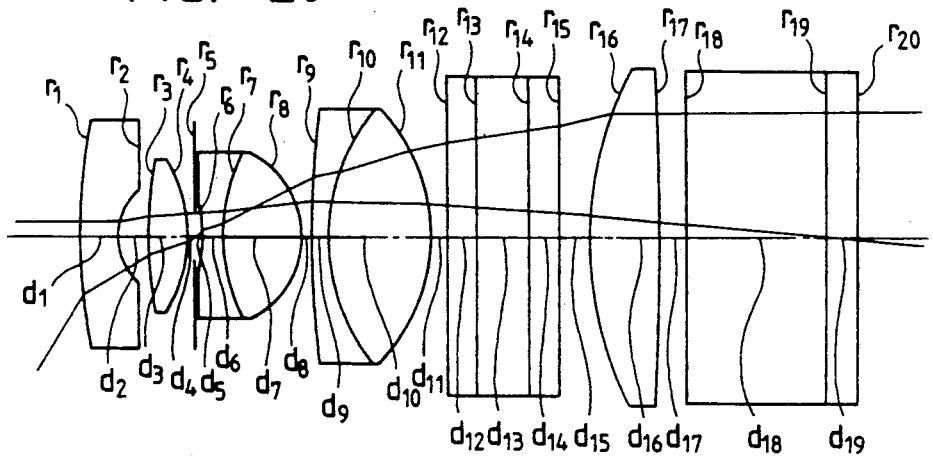
Figure 21:
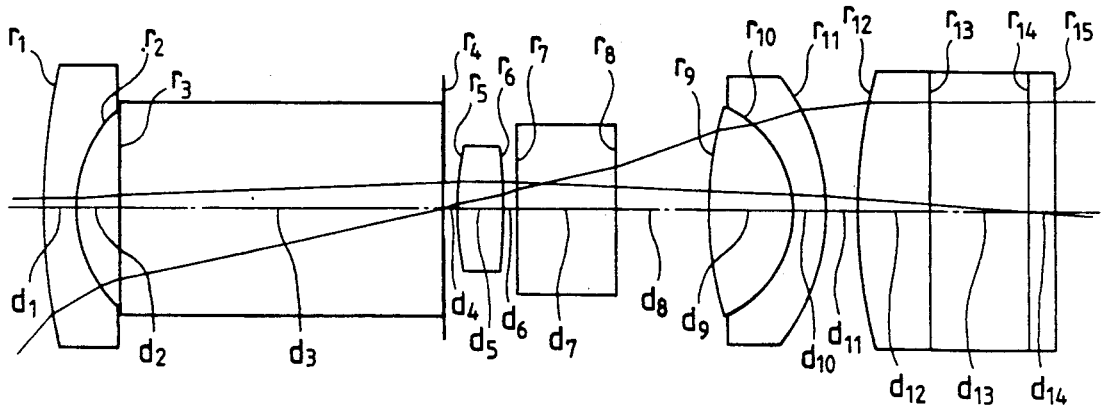
Figure 22:
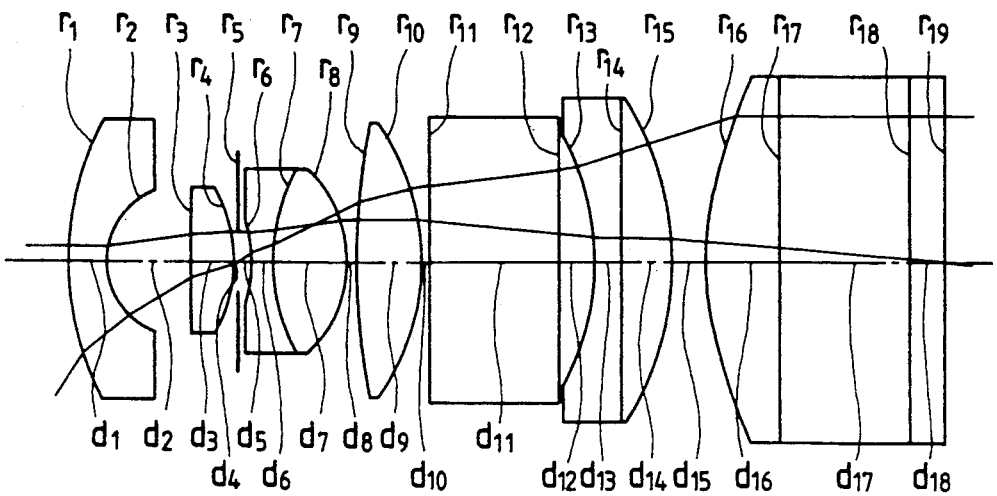
Figure 23:
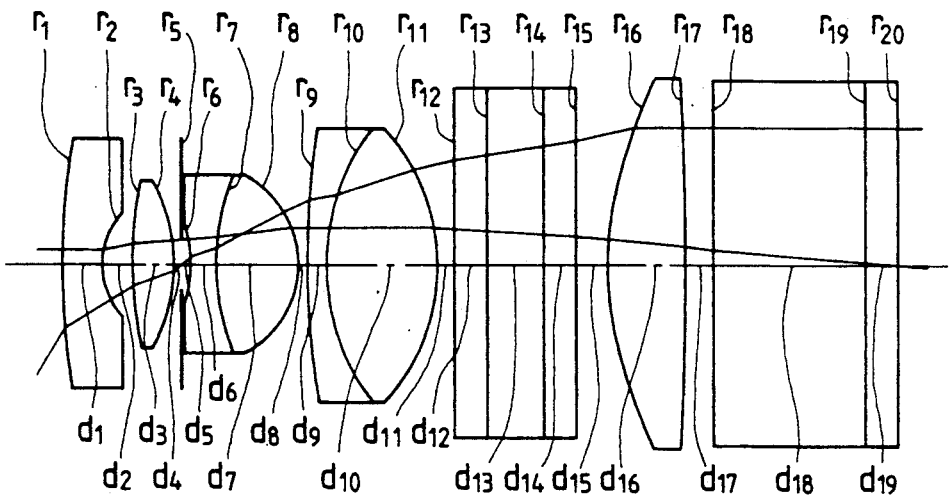
Figure 24:
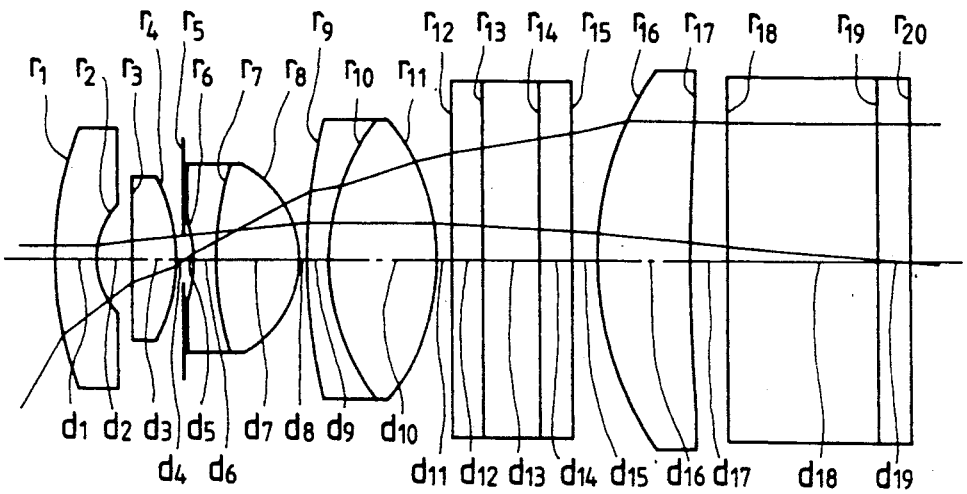
Figure 25:
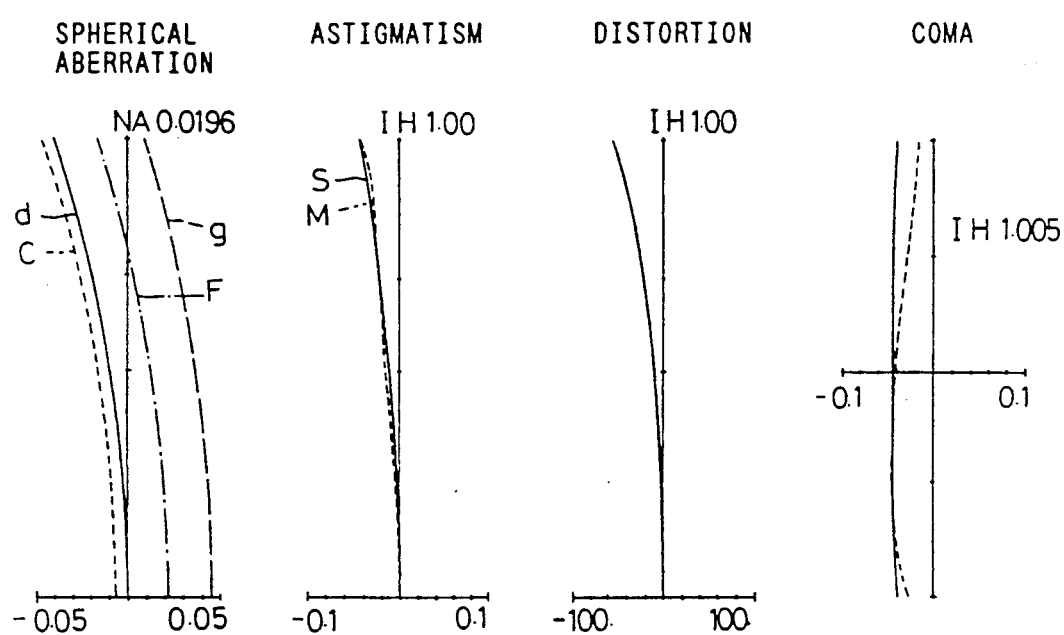
Figure 26:
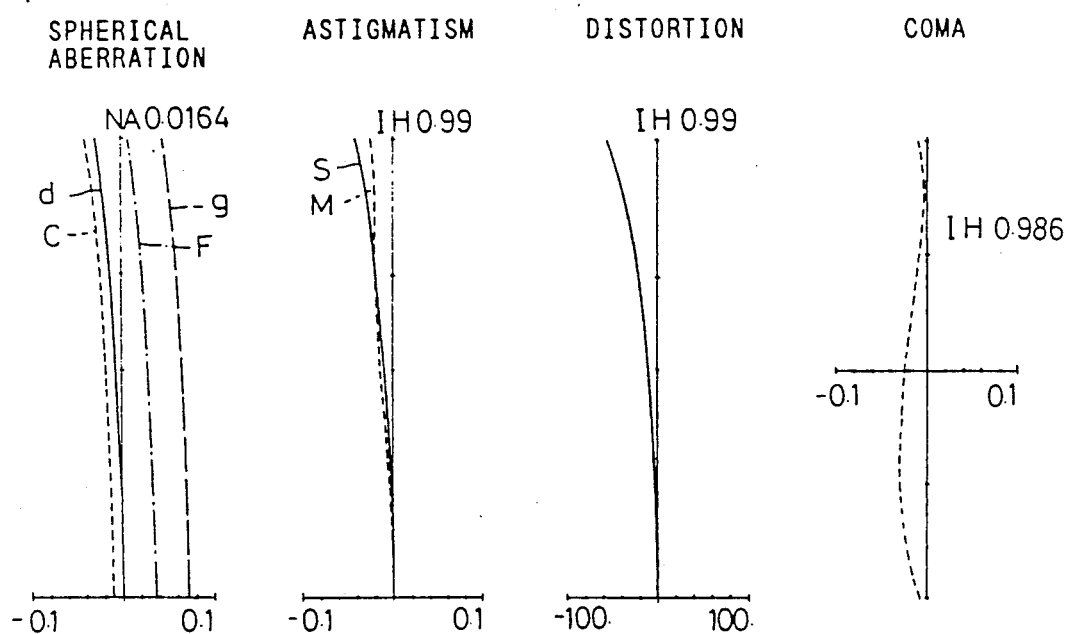
Figure 27:
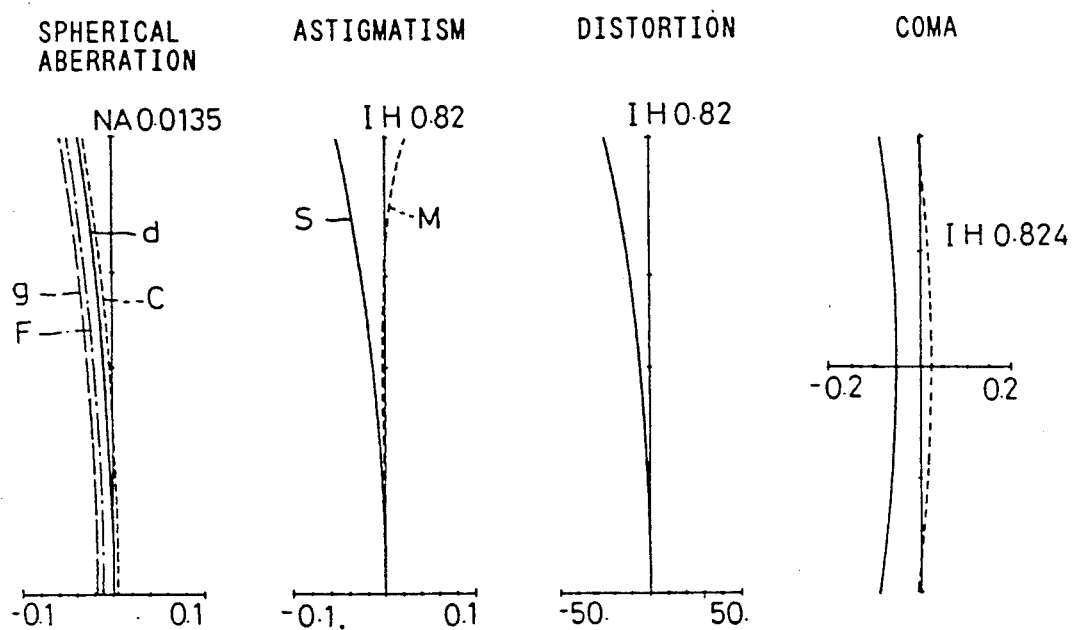
Figure 28:
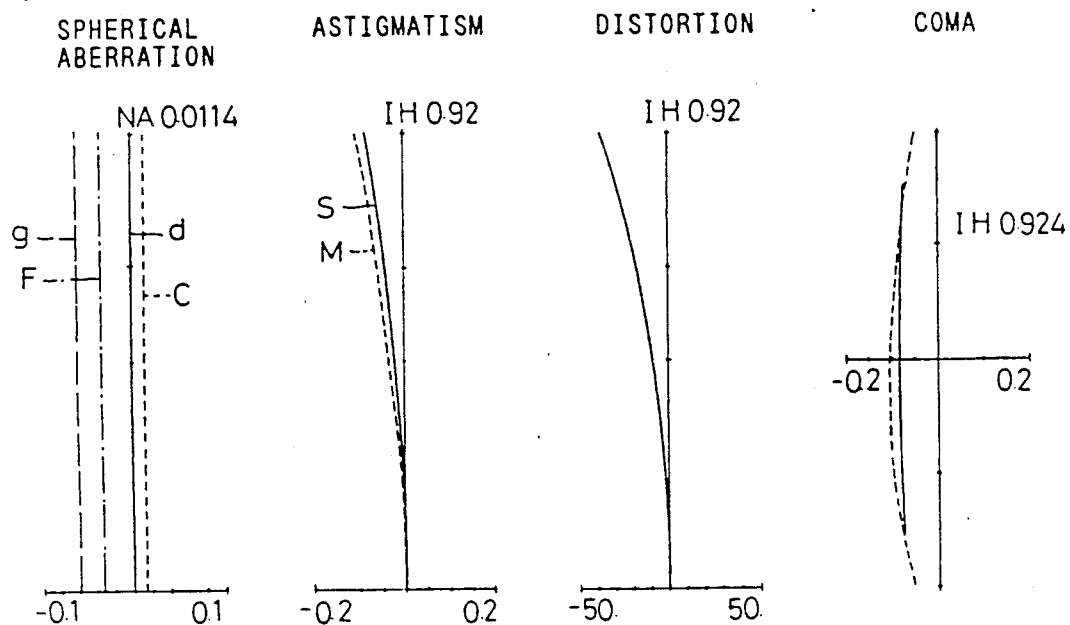
Figure 31:
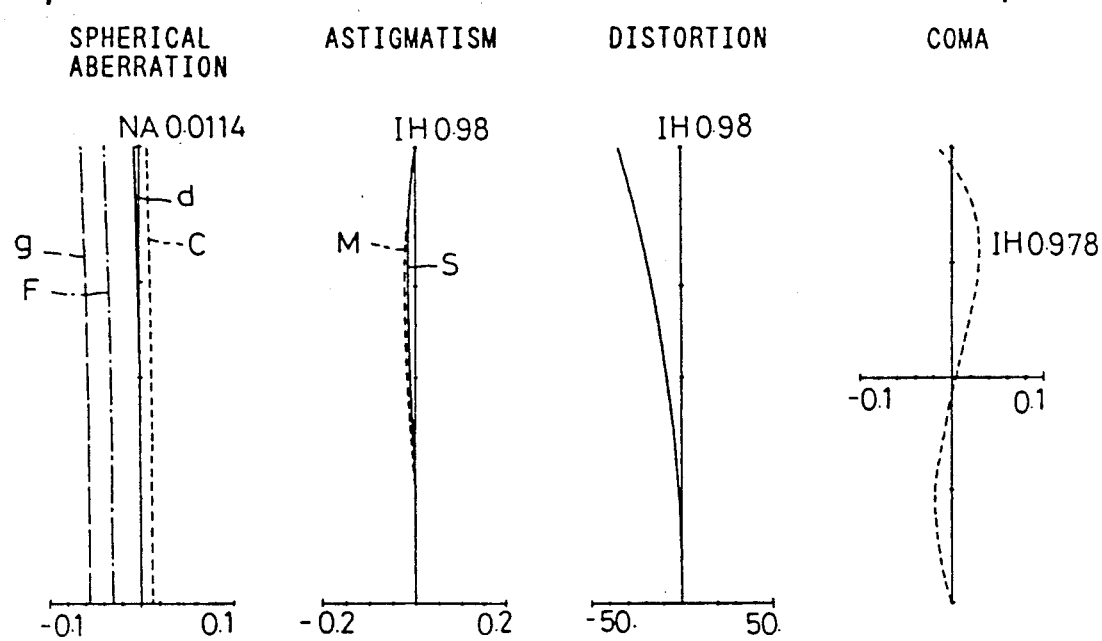
Figure 32:
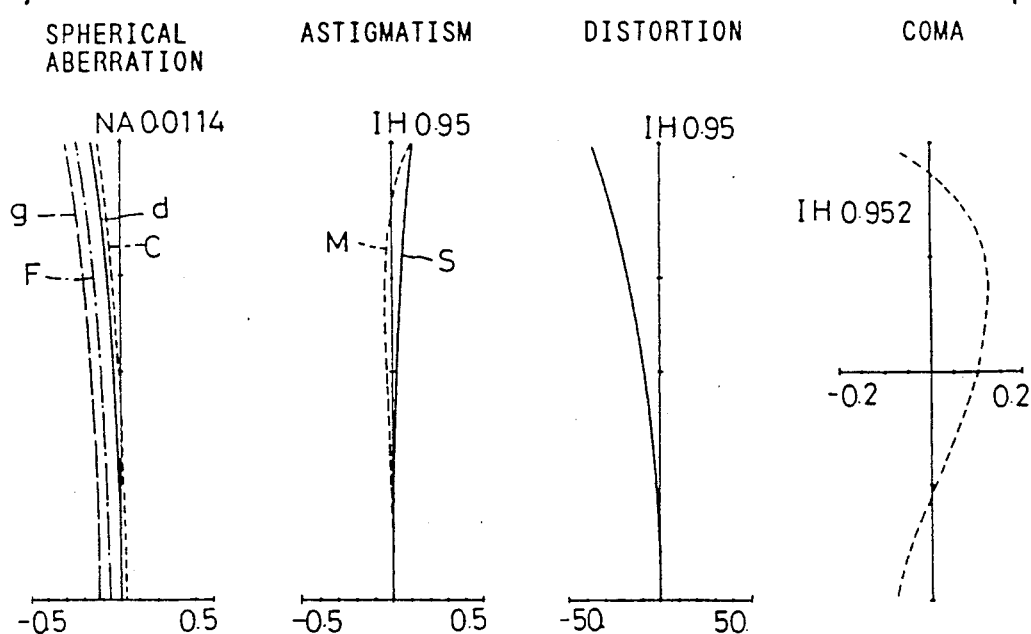
Figure 33:
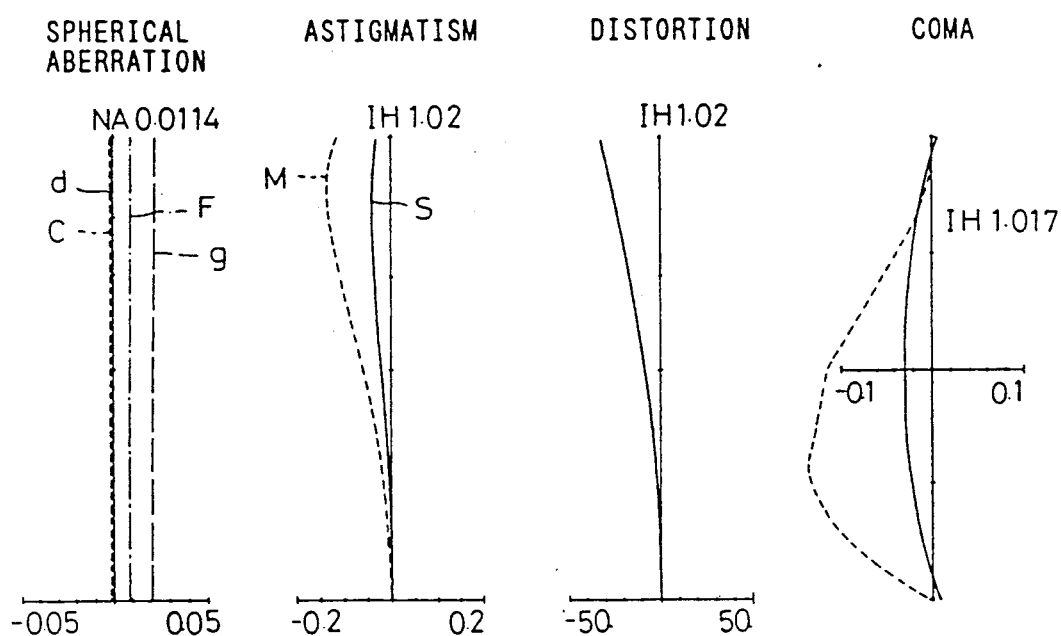
Figure 34:
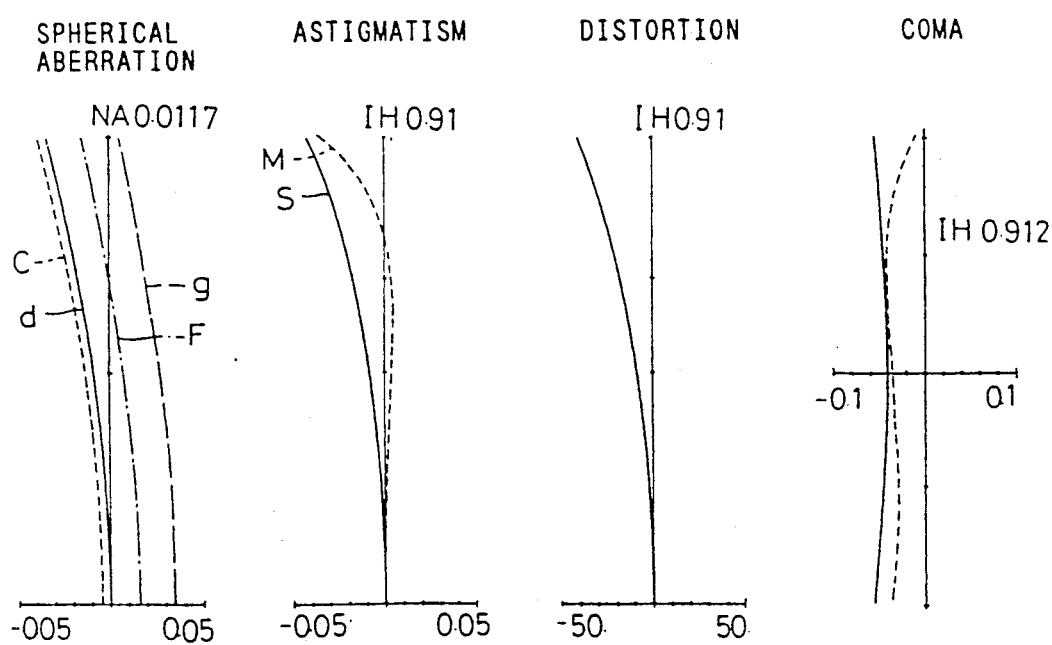
Figure 35:
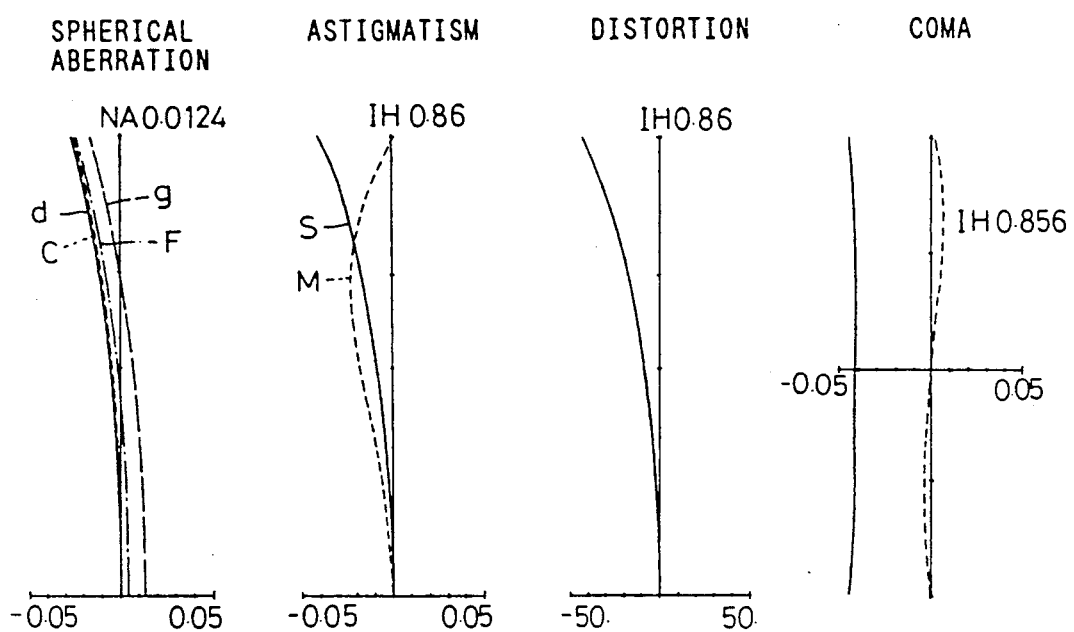
Figure 36:
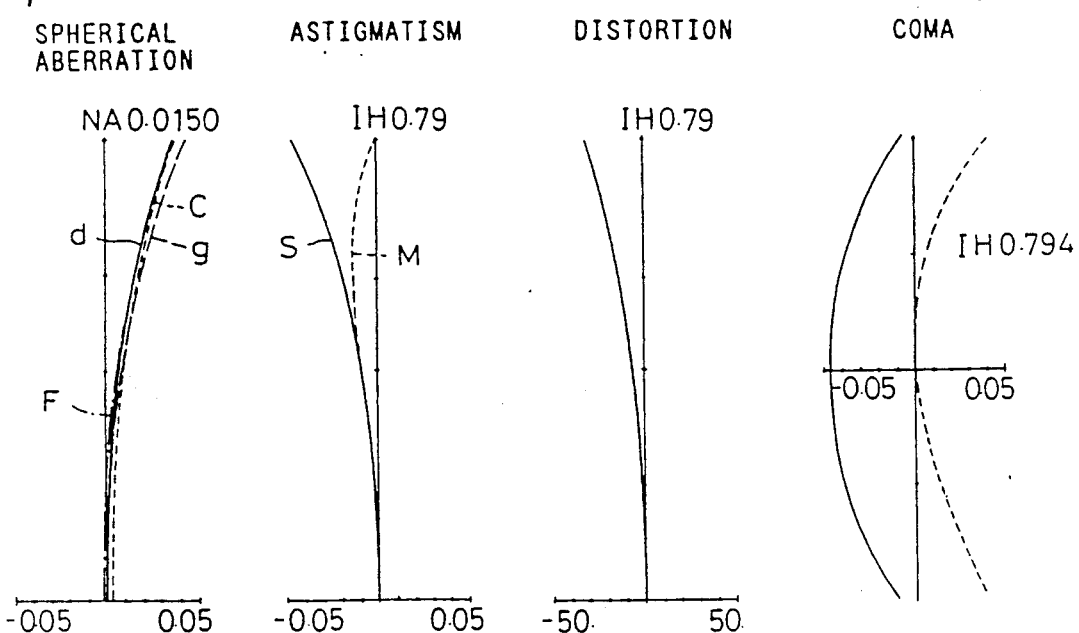
Figure 37:
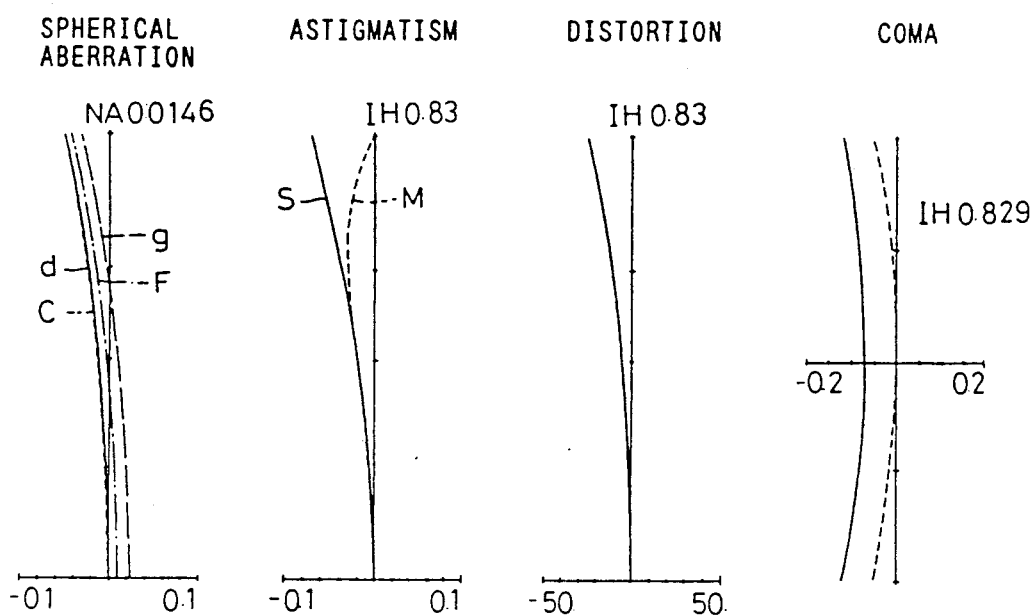
Figure 38:
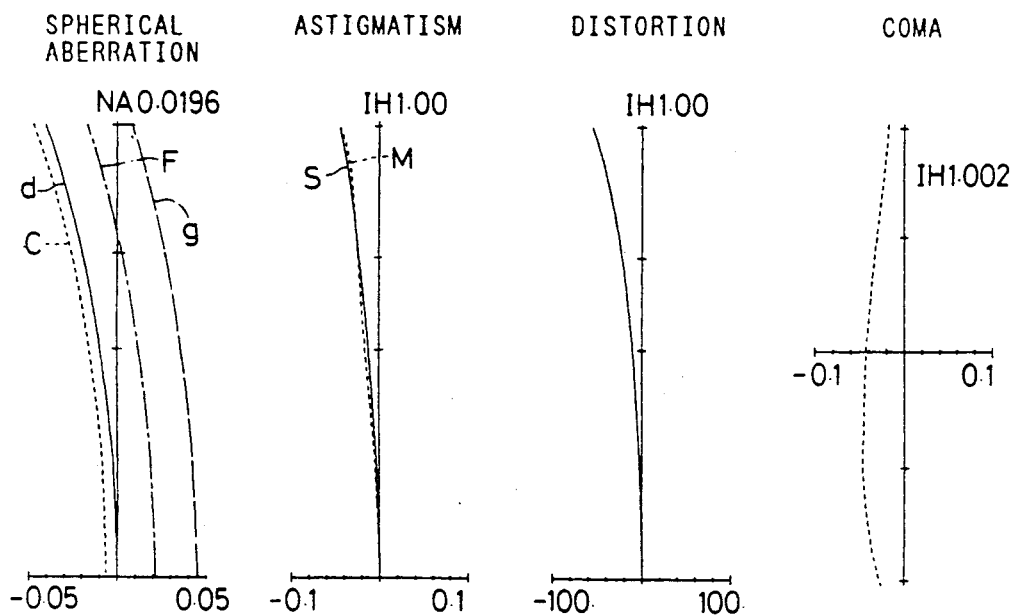
Figure 39:
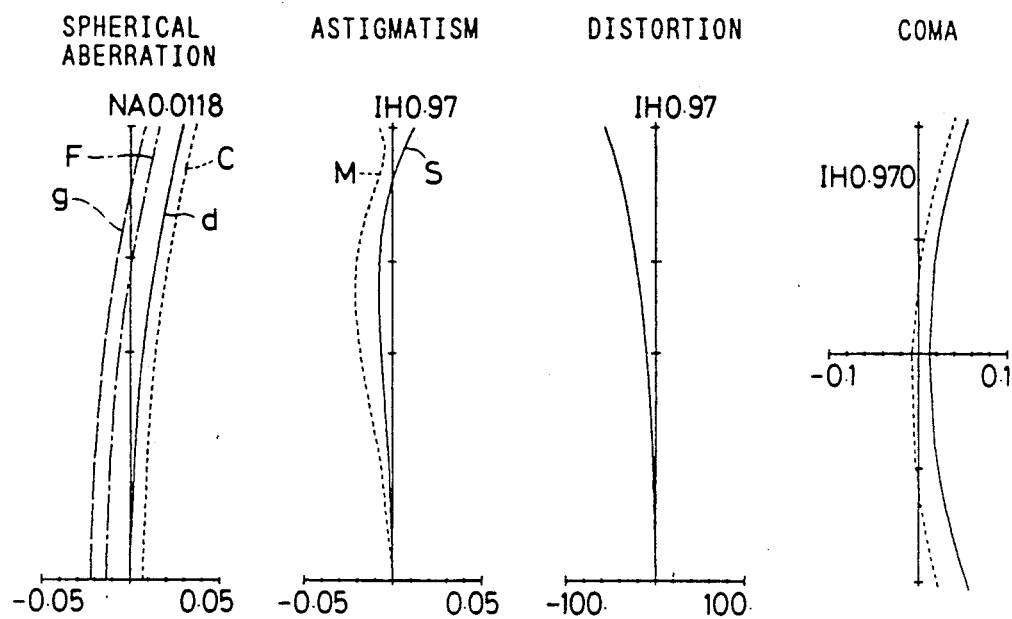
Figure 40:
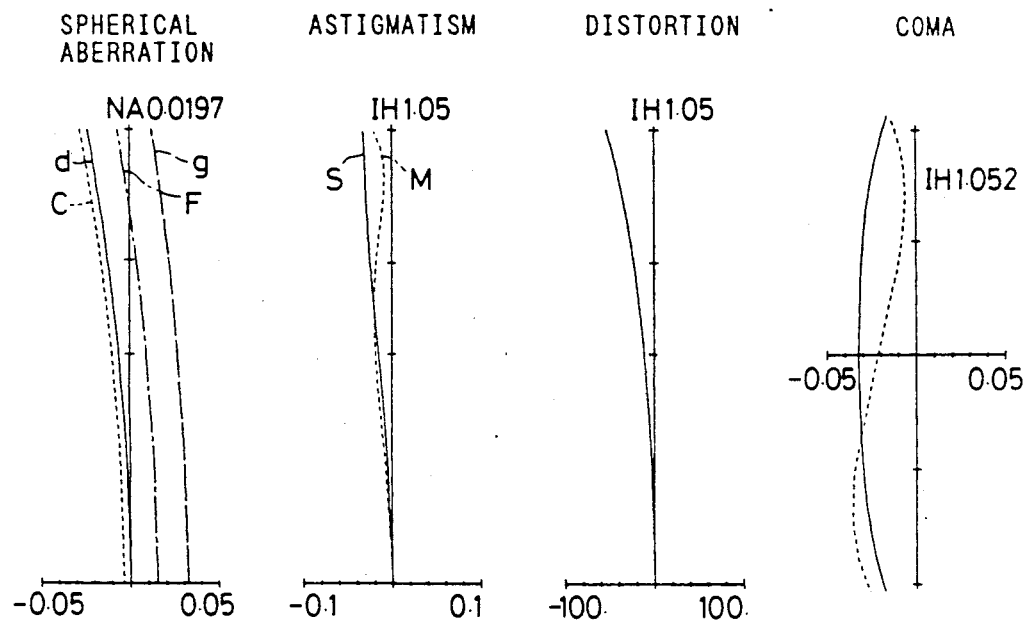
Figure 41:
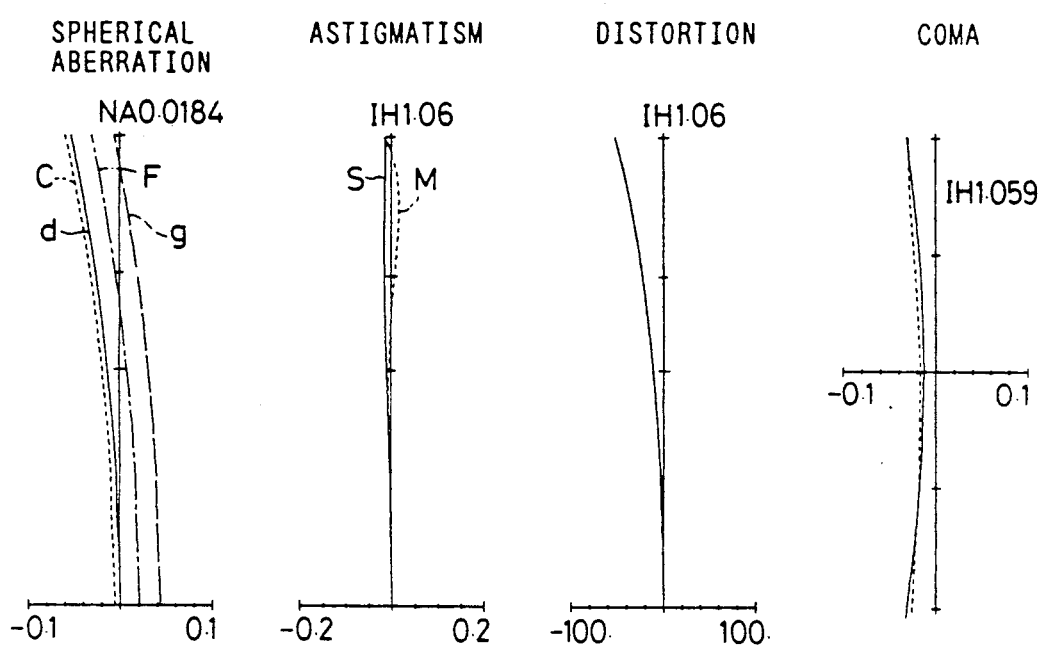
Figure 42:
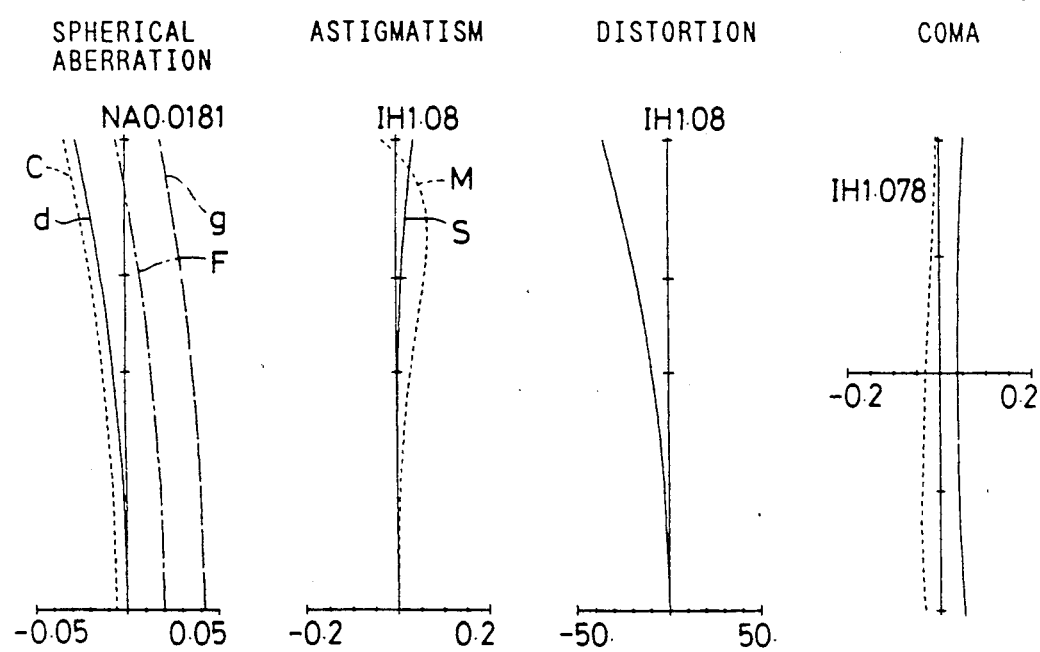
Figure 43:
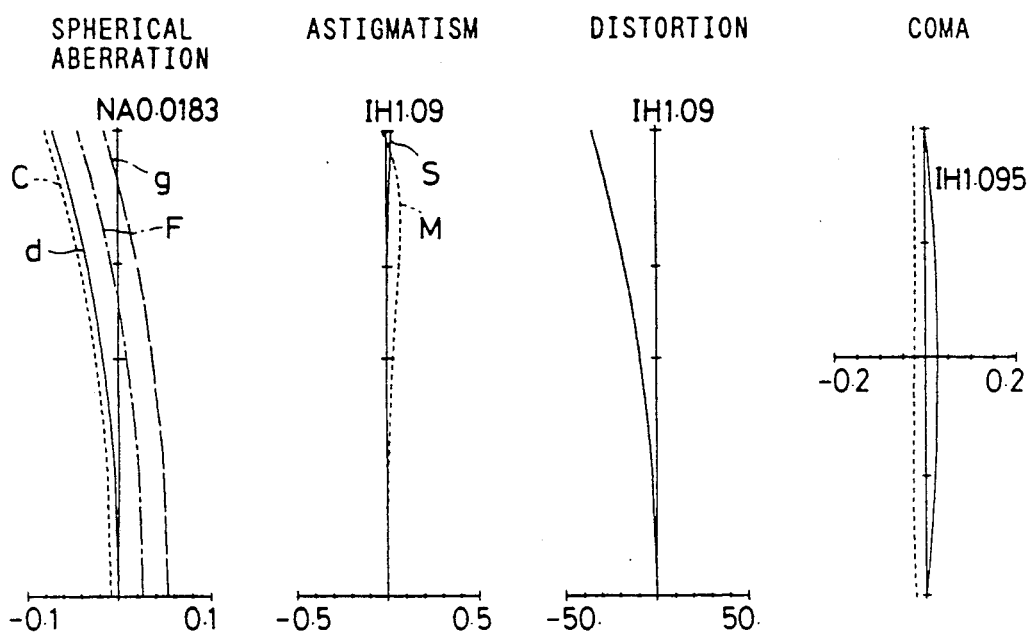
Figure 44:
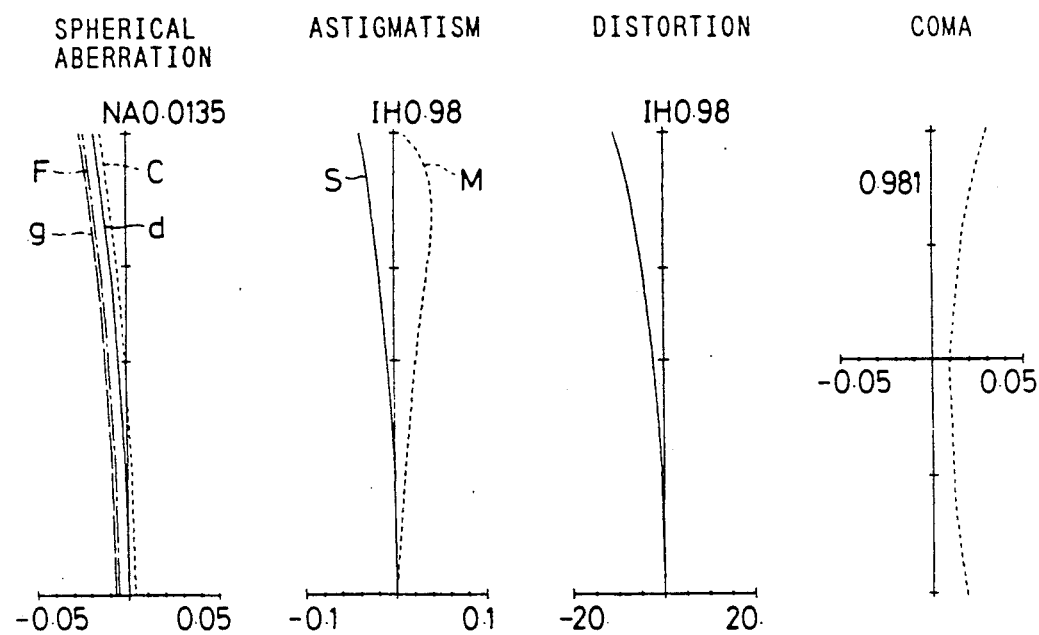
Figure 45:
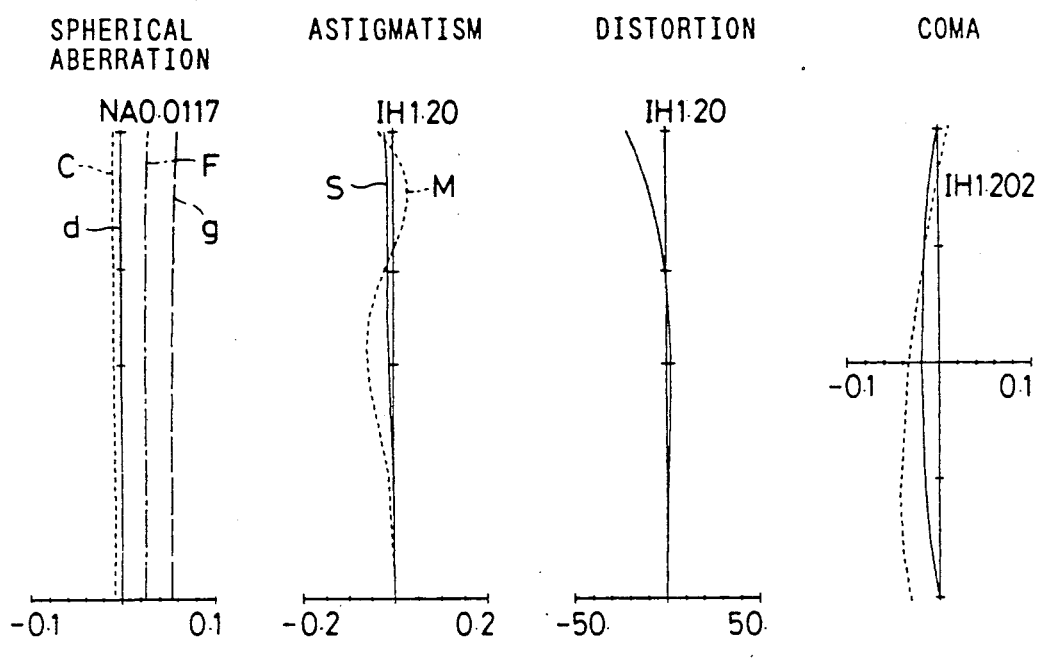
Figure 46:
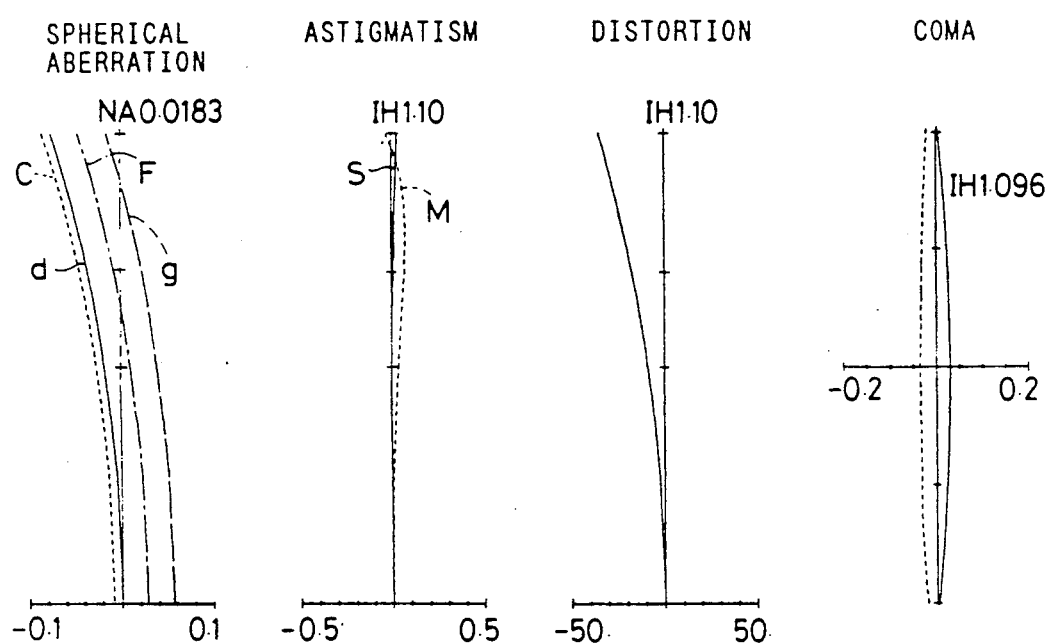
Figure 47:
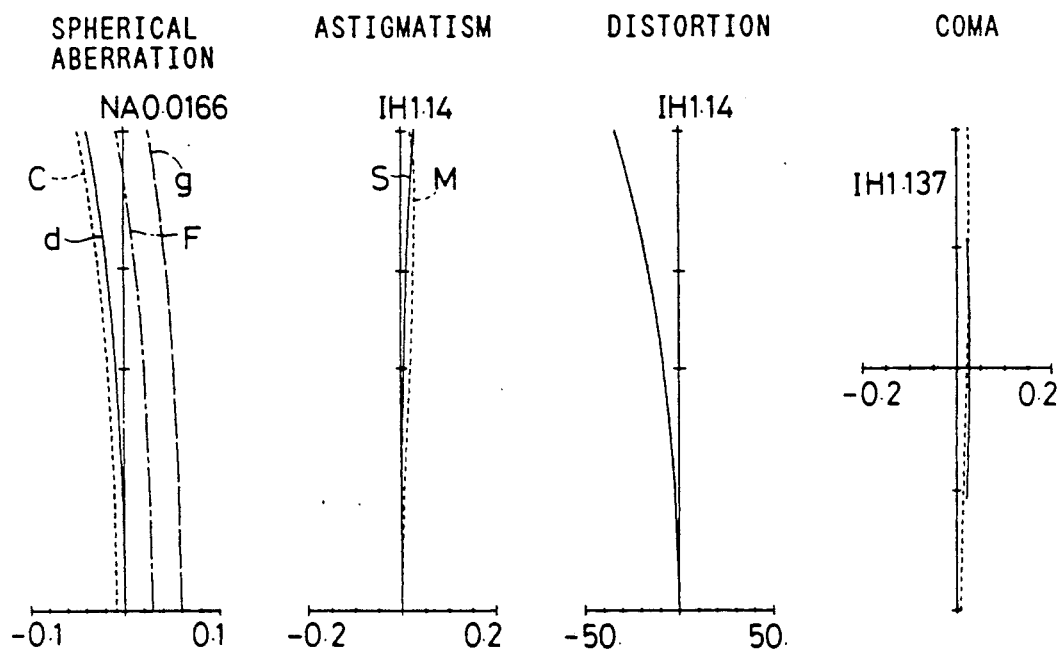

The Embodiment 14 has the composition illustrated in FIG. 15 which is similar to the composition of the Embodiment 1 but is different in arrangement of the filter from the Embodiment 1. An optical system for medical endoscopes, for example, may comprise a YAG cut filter for carrying out medical treatment with YAG laser, etc. Since this filter has high reflectance for visible rays, it may produce, depending on the location thereof, ghost and/or flare by reflecting the rays which are reflected from an image pickup device. When the filter is arranged on the image side of the field lens component $L_F$, i.e., at a location where the principal ray is incident perpendicularly on the image pickup device, as in the Embodiment 14, the rays reflected on the filter surface return correctly to the original positions on the image pickup device and can hardly produce ghost or flare.

In the Embodiment 15, all the filters which are arranged on the object side and image side of the field lens component $L_F$ in the other Embodiments are arranged on the image side of the field lens component $L_F$. This design allows the filters to hardly produce ghost and/or flare, and makes the principal ray incident nearly perpendicularly on all the filters, thereby making it possible to prevent the filter characteristics from being changed by large angles of incidence on the filters.

In the Embodiment 16, the image side surface of the field lens component $L_F$ is designed as an aspherical surface so that rays are incident nearly perpendicularly on the image surface at all the image heights.

In the Embodiment 17, the object side surface of the field lens component $L_F$ is designed as an aspherical surface so that rays are incident nearly perpendicularly on the image surface at all the image heights.

In the Embodiment 18, the image side surface of the field lens component $L_F$ and the first surface of the optical system are designed as aspherical surfaces respectively for perpendicular incidence on the image surface and correction of distortion.

In the Embodiment 19, the object side surface of the field lens component $L_F$ and the first surface of the optical system are designed as aspherical surfaces respectively for perpendicular incidence on the image surface and correction of distortion.

In each of the Embodiments 20 and 21, a field lens $L_F$ having an aspherical surface on the object side is integrated with an image pickup device. This design narrows the airspace reserved between the field lens component $L_F$ and the image pickup device and lowers height of ray on the field lens component $L_F$, thereby making it possible to make the optical system thinner.

Further, the Embodiment 20 comprises an airspace for allowing to arrange a field direction changing prism on the object side of the aperture stop. In addition, the Embodiment 21 is of a forward viewing type and comprises an afocal section in the rear subsystem thereof.

Each of the Embodiments 22 and 23 comprises three aspherical surfaces. In the Embodiment 22, the field lens component $L_F$ is separate from an image pickup device and both the surfaces of the field lens component $L_F$ are designed as aspherical surfaces. In the Embodiment 23, only the object side surface of the field lens component $L_F$ is designed as an aspherical surface since the field lens component having aspherical surfaces on both the sides requires tedious techniques for shaping. In addition, the Embodiment 23 comprises another aspherical surface in the rear subsystem thereof.

The Embodiments 1 through 23 have the compositions illustrated in FIG. 2 through FIG. 24.

In each of these Embodiments, the plane parallel plates arranged in the optical system are, in the order from the object side, an infrared cut filter for eliminating the rays in the infrared region and an optical low pass filter for preventing moire from being produced when a mosaic type solid-state image pickup device is used. The infrared cut filter may be an interference filter or an absorption filter which may be coated or not coated. The filter may further be a cut filter which eliminates the rays having the wavelength other than those for the ordinary observation.

Further, it is possible to replace the locations between the optical low pass filter and the cut filter, or combine these filters into a single filter.

Though the Embodiments described above use the mosaic type solid-state image pickup devices, the optical systems are applicable also to fiberscopes as well as endoscopes using the solid-state image pickup devices of field sequential color system and other types of image pickup devices.

The optical system for endoscopes according to the present invention has a short total length, a small outside diameter and is suited for use with endoscopes. Further, even when the optical system for endoscopes is combined with the mosaic type solid-state image pickup device, the optical system is capable of forming images of high quality which are not affected by the color shading or moiré. Moreover, the optical system for endoscopes according to the present invention is so designed, by using aspherical surfaces, as to prevent the color shading more effectively and have aberrations, especially distortion, favorably corrected even at a wide field angle.

We claim:

1. An optical system for endoscopes comprising:
   an imaging lens system including a plurality of lens components and having an aperture stop arranged within said lens components, and
   a field lens component arranged on an image side of said imaging lens system,
   wherein said optical system for endoscopes includes a negative lens component and a positive lens component arranged on an object side of said aperture stop,
   wherein lens components arranged on the image side of said aperture stop comprise a substantially telecentric optical system, and said optical system for endoscopes satisfying the following condition (1):

$$f_F < 10f \qquad (1)$$

wherein the reference symbol $f_F$ represents focal length of the field lens component and the reference symbol f designates focal length of the optical system as a whole.

2. An optical system for endoscopes comprising:
an imaging lens system including a plurality of lens components and an aperture stop arranged within said lens components, and
a field lens component arranged on an image side of said imaging lens system,
wherein said optical system for endoscopes comprises a negative lens component and an optical element having a planar surface of incidence and a planar surface of emergence arranged in this order before said aperture stop, and the lens components arranged on the image side of said aperture stop include a substantially telecentric optical system, and
said optical system for endoscopes satisfying the following condition (1):

$$f_F < 10f \tag{1}$$

wherein the reference symbol $f_F$ represents focal length of the field lens component and the reference symbol f designates focal length of the optical system as a whole.

3. An optical system for endoscopes according to claim 1 or 2, wherein an optical path length as measured from said aperture stop to said field lens component satisfies the following condition (2):

$$D_1 > 0.2f \tag{2}$$

wherein the reference symbol $D_1$ represents the optical path length between said aperture stop and said field lens component.

4. An optical system for endoscopes comprising:
an imaging lens system including a plurality of lens components and an aperture stop arranged within said lens components, and
a field lens component arranged on an image side of said imaging lens system,
wherein an aspherical surface including portions having a refractive function that is weakened as the portions are farther from an optical axis toward a margin being arranged on said field lens component,
said optical system for endoscopes satisfying the following condition (1):

$$f_F < 10f \tag{1}$$

wherein the reference symbol $f_F$ represents focal length of the field lens component and the reference symbol f designates focal length of the optical system as a whole.

5. An optical system for endoscopes comprising:
an imaging lens system including a plurality of lens components and an aperture stop, and
a field lens component arranged on an image side of said imaging lens system,
wherein an aspherical surface including portions having a refractive function that is weakened as the portions are farther from an optical axis toward a margin being arranged on optical element located in the vicinity of said field lens component, and said optical system for endoscopes satisfying the following condition (1):

$$f_F < 10f \tag{1}$$

wherein the reference symbol $f_F$ represents focal length of the field lens component and the reference symbol f designates focal length of the optical system as a whole.

6. An optical system for endoscopes according to claim 1, 2, 4 or 5, wherein an optical path length as measured from said field lens component to an image surface satisfies the following condition:

$$0.3 < D_2 < 5f \tag{3}$$

wherein the reference symbol $D_2$ represents the optical path length as measured from a vertex on an image side surface of said field lens component to the image surface.

7. An optical system for endoscopes according to claim 1, 2, 4, or 5 further comprising an image pickup device integrated with said field lens component and satisfying the following conditions (3'):

$$0.3 < D_2 < 5f \tag{3'}$$

wherein the reference symbol $D_2$ represents the optical path length as measured from a vertex on an image side surface of said field lens component to the image pickup device.

8. An optical system for endoscopes according to claim 1, 2, 4 or 5 further comprising a plane parallel plate arranged on an object side of said field lens component and, when the lens systems located on the object side and the image side of said plane parallel plate are referred to as a front subsystem and a rear subsystem, respectively the optical system satisfying the following conditions (4) through (6):

$$f_1 > 0.3f \tag{4}$$

$$|f_n| < 4f \tag{5}$$

$$0.3f < f_p < 5f \tag{6}$$

wherein the reference symbol $f_1$ represents focal length of said front subsystem, the reference symbol $f_n$ designates focal length of the negative lens component arranged in said front subsystem and the reference symbol $f_p$ denotes total focal length of the lens elements other than the negative lens elements in the front subsystem.

9. An optical system endoscopes according to claim 8, wherein said rear subsystem comprises a nearly afocal section.

10. An optical system for endoscopes according to claim 9 wherein said nearly afocal section comprises a positive lens component and a negative lens component, and satisfies the following condition (7):

$$f_{ap}/f_{an} < -0.1 \tag{7}$$

wherein the reference symbol $f_{ap}$ and $f_{an}$ represent focal lengths of the lens component having positive refractive power and the lens component having negative refractive power, respectively, in said nearly afocal section.

11. An optical system for endoscopes according to claim 9 wherein said nearly afocal section is arranged in said rear subsystem and satisfies the following condition (8):

$$-40f < f_{an} < -0.2f \quad (8)$$

wherein the reference symbol $f_{an}$ represents focal length of the lens component having negative refractive power in the nearly afocal section.

12. An optical system for endoscopes comprising:
an imaging lens system including a plurality of lens components and an aperture stop arranged within said lens components, and
a field lens component arranged on the image side of said imaging lens system,
wherein said optical system for endoscopes comprising a negative lens component arranged before said aperture stop, and
wherein an aspherical surface including portions having a refractive function that is weakened as the portions are farther from an optical axis toward a margin being arranged on said field lens component,
said optical system for endoscopes satisfying the following condition (1):

$$f_F < 10f \quad (1)$$

wherein the reference symbol $f_F$ represents focal length of the field lens component and the reference symbol f designates focal length of the optical system as a whole.

* * * * *